(12) United States Patent
Morimura et al.

(10) Patent No.: US 7,606,399 B2
(45) Date of Patent: Oct. 20, 2009

(54) SURFACE SHAPE RECOGNIZING SENSOR DEVICE

(75) Inventors: Hiroki Morimura, Tokyo (JP); Mamoru Nakanishi, Tokyo (JP); Satoshi Shigematsu, Tokyo (JP); Takahiro Hatano, Tokyo (JP); Yukio Okazaki, Tokyo (JP); Katsuyuki Machida, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 703 days.

(21) Appl. No.: 10/582,128

(22) PCT Filed: Jul. 15, 2005

(86) PCT No.: PCT/JP2005/013151

§ 371 (c)(1),
(2), (4) Date: Jun. 6, 2006

(87) PCT Pub. No.: WO2006/009110

PCT Pub. Date: Jan. 26, 2006

(65) Prior Publication Data

US 2008/0056543 A1 Mar. 6, 2008

(30) Foreign Application Priority Data

Jul. 23, 2004 (JP) ............................. 2004-215543

(51) Int. Cl.
*G06K 9/00* (2006.01)
(52) U.S. Cl. ................. 382/124; 382/125; 702/104; 438/48; 340/5.83
(58) Field of Classification Search ............... 382/124, 382/127, 115, 116, 125, 126, 299; 702/104, 702/130, 100; 340/5.83; 438/48, 50; 356/71; 307/125; 257/414, 415, 416, 417; 178/18.05; 345/161; 341/33; 200/343; 250/556
See application file for complete search history.

(56) References Cited

U.S. PATENT DOCUMENTS 6,556,935 B2 * 4/2003 Morimura et al. ........... 702/104

(Continued)

FOREIGN PATENT DOCUMENTS

JP 04-231803 A 8/1992

(Continued)

OTHER PUBLICATIONS

Inglis et al., "A Robust, 1.8V 250μW Direct-Contact 500dpi Fingerprint Sensor", ISSCC Digest of Technical Papers, Feb. 1998, pp. 284-285.

*Primary Examiner*—Sheela C Chawan
(74) *Attorney, Agent, or Firm*—Blakely, Sokoloff, Taylor & Zafman LLP

(57) ABSTRACT

A sensor cell includes a sensor electrode (101) formed on a substrate (100), a signal output unit (16) which outputs a signal corresponding to a capacitance (Cf) formed between the sensor electrode and the surface of a finger (3), a high-sensitivity electrode (103) formed on the substrate so as to be insulated and isolated from the sensor electrode, and a potential controller (14) which controls the potential of the finger surface via a capacitance (Cc) formed between the high-sensitivity electrode and the finger surface by controlling the potential of the high-sensitivity electrode. In this arrangement, when the resistance of the finger is high, the potential of the finger surface can be controlled so as not to fluctuate with the potential change of the sensor electrode. This makes it possible to increase the sensitivity of detection of the capacitance formed between the sensor electrode and the finger surface, so ridges and valleys of the finger surface can be clearly discriminated by outputs from a plurality of sensor cells.

17 Claims, 19 Drawing Sheets

U.S. PATENT DOCUMENTS

| | | | |
|---|---|---|---|
| 6,831,980 B1 * | 12/2004 | Borza et al. | 380/46 |
| 6,917,694 B1 * | 7/2005 | Machida et al. | 382/124 |
| 6,987,871 B2 * | 1/2006 | Kalnitsky et al. | 382/124 |
| 7,062,075 B2 * | 6/2006 | Morimura et al. | 382/124 |
| 7,123,026 B2 * | 10/2006 | Sato et al. | 324/658 |
| 2004/0021786 A1 * | 2/2004 | Nakamura et al. | 348/294 |

FOREIGN PATENT DOCUMENTS

| | | |
|---|---|---|
| JP | 2000-065514 A | 3/2000 |
| JP | 2000-346608 A | 12/2000 |
| JP | 2002-062108 A | 2/2002 |

* cited by examiner

SURFACE SHAPE RECOGNIZING SENSOR DEVICE

The present patent application is a non-provisional application of International Application No. PCT/JP2005/013151, filed Jul. 15, 2005.

TECHNICAL FIELD

The present invention relates to a surface shape recognizing sensor device and, more particularly, to a surface shape recognizing sensor device which senses fine ridges and valleys of, e.g., fingerprints of humans and noseprints of animals.

BACKGROUND ART

A sensor which particularly senses fingerprints is reported as a sensor for recognizing a surface shape having fine ridges and valleys. Also, as a technique for detecting fingerprint patterns, a capacitive fingerprint sensor using the LSI fabrication technique is proposed. Examples of the capacitive fingerprint sensor are described in reference 1 (Japanese Patent Laid-Open No. 2000-346608) and reference 2 ("A Robust, 1.8 V 250 µW Direct-Contact 500 dpi Fingerprint Sensor", ISSCC DIGEST OF TECHNICAL PAPERS, February 1998, pp. 284-285).

As shown in FIG. 18, each of these capacitive fingerprint sensors is formed as a sensor cell array 2 in which sensor cells 1 are two-dimensionally arrayed on an LSI chip, and detects the capacitance formed between a sensor electrode of each sensor cell 1 and the skin of a finger 3 which comes in contact with the sensor electrode via an insulating passivation film, thereby sensing the pattern of ridges and valleys of the fingerprint. Since the value of the capacitance changes in accordance with a ridge or valley of a fingertip skin surface, a ridge or valley of a fingertip skin surface can be sensed by detecting this fine capacitance difference.

As shown in FIG. 19, a sensor electrode 101 is incorporated into each sensor cell 1 of the sensor cell array 2.

A surface shape recognizing sensor device as the first prior art using the principle of the capacitive fingerprint sensor shown in FIG. 18 will be explained with reference to FIG. 20. In the surface shape recognizing sensor device shown in FIG. 20, each sensor cell 1 comprises a detecting element 10, signal generating circuit 11, switch SW1, and detection circuit 12.

The detecting element 10 includes an insulating layer 100 on a substrate, a sensor electrode 101 formed on the insulating layer 100, and a passivation film 102 so formed as to cover the sensor electrode 101.

The signal generating circuit 11 includes a switch SW2 which generates a voltage signal corresponding to a capacitance Cf formed between the sensor electrode 101 and the skin of a finger 3 in contact with the passivation film 102, and a current source 110. The detection circuit 12 detects the voltage signal from the signal generating circuit 11. The switch SW1 supplies a potential Vp to a node N1 as a connecting point between the sensor electrode 101 of the detecting element 10 and the output terminal of the signal generating circuit 11. Note that Cp in FIG. 20 denotes a parasitic capacitance.

Since the capacitance Cf is determined by the distance between the sensor electrode 101 and the skin of the finger 3, the value of Cf changes in accordance with a ridge or valley of a fingerprint. Accordingly, a voltage signal corresponding to a ridge or valley of the finger 3 is output from the signal generating circuit 11 to the node N1. This voltage signal is detected as a signal reflecting the ridge or valley of the fingerprint by the detection circuit 12, and as a consequence the fingerprint pattern is detected.

A normal operation of the surface shape recognizing sensor device shown in FIG. 20 will be explained with reference to FIGS. 21A to 21D. The surface of the finger 3 is connected to the ground potential (GND) via a resistance Rf of the finger 3. Assume that Rf=0Ω. Accordingly, the potential of the finger surface, i.e., the potential at a node N2 is held at the ground potential (FIG. 21D).

Initially, a control signal P for controlling opening/closure of the switch SW1 is Low level (FIG. 21A). A control signal S1 for controlling opening/closure of the switch SW2 is also Low level (FIG. 21B). Therefore, both the switches SW1 and SW2 are open. In this case, the potential at the node N1 is equal to or lower than the potential Vp (FIG. 21C).

In this state, if the control signal P changes from Low level to High level at time t1 in FIG. 21A, the switch SW1 is closed and turned on, and consequently the potential at the node N1 is precharged to the potential Vp (FIG. 21C).

After the precharge is completed, the control signal P changes to Low level at time t2 in FIG. 21A, and simultaneously the control signal S1 changes to High level as shown in FIG. 21B. Accordingly, the switch SW1 is turned off, the switch SW2 is turned on, and the electric charge stored in the node N1 is extracted by the current source 110. As a consequence, the potential (voltage signal) at the node N1 lowers (FIG. 21C). Letting Δt be a High-level period of the control signal S1, a potential drop ΔV of the node N1 from the potential Vp when Δt has elapsed is given by $$\Delta V = I \Delta t / (Cf + Cp) \quad (1)$$

where I is the current value of the current source 110, and Cp is a parasitic capacitance.

Since the electric current I, period Δt, and parasitic capacitance Cp are constant, the potential drop ΔV is determined by the capacitance Cf. The capacitance Cf is determined by the distance between the sensor electrode 101 of the detecting element 10 and the skin of the finger 3, so the value of the capacitance Cf changes in accordance with a ridge or valley of a fingertip skin surface. Accordingly, the change in magnitude of the potential drop ΔV reflects a ridge or valley of a fingertip skin surface. That is, letting Cfv be the capacitance formed between a valley of a fingertip skin surface and the sensor electrode 101 and Cfr be the capacitance formed between a ridge of a fingertip skin surface and the sensor electrode 101, a difference ΔVi between a voltage signal corresponding to a valley of a fingertip skin surface and a voltage signal corresponding to a ridge of a fingertip skin surface is given by $$\Delta Vi = I \Delta t / (Cfv + Cp) - I \Delta t / (Cfr + Cp) \quad (2)$$

Since, therefore, the voltage signal detected by the detection circuit 12 of each sensor cell is a signal reflecting a ridge or valley of a fingertip skin surface, ridges and valleys of a fingertip skin surface can be discriminated by outputs from a plurality of sensor cells.

The surface of the finger 3, however, is connected to the ground potential via the resistance Rf of the finger 3, so no sufficiently large voltage difference ΔVi can be obtained in some cases if the resistance Rf is high because, e.g., the finger 3 is dry. The operation of the surface shape recognizing sensor device when Rf>>0 will be explained with reference to FIGS. 22A to 22D.

The basic operation timings in FIGS. 22A to 22D are the same as in FIGS. 21A to 21D. On a ridge of a fingerprint, however, the potential of the finger surface, i.e., the potential at the node N2 cannot hold the ground potential and fluctuates as shown in FIG. 22D with the potential change at the node N1 shown in FIG. 22C. Consequently, the value of the capacitance Cf formed between the ridge of the fingertip skin surface and the sensor electrode 101 effectively decreases (Cf=αCfr, α<1), and as a result the voltage difference ΔVi (=IΔt/(Cfv+Cp)−IΔt/(α·Cfr+Cp)) decreases as shown in FIG. 22C. This makes it difficult for the surface shape recognizing sensor device shown in FIG. 20 to discriminate between the ridge and valley patterns of a fingerprint image, and consequently no clear fingerprint image pattern can be obtained.

A surface shape recognizing sensor device as the second prior art using the principle of the capacitive fingerprint sensor shown in FIG. 18 will be explained with reference to FIG. 23.

This surface shape recognizing sensor device differs from the example shown in FIG. 20 in the arrangement of a signal generating circuit 13. The signal generating circuit 13 includes a switch SW3 which selects and outputs a power supply potential VDD or ground potential GND, and a capacitive element Cs formed between the output terminal of the switch SW3 and a node N1. The signal generating circuit 13 extracts an electric charge from the node Ni by charging/discharging the capacitive element Cs, and the charge amount to be extracted is controlled by the capacitance value of Cs and a driving voltage Vs of Cs. In this device, the charge amount to be extracted from the node N1 is controlled by setting the driving voltage Vs shown in FIG. 23 at the power supply potential VDD (VDD>0) or ground potential GND via the switch SW3.

A normal operation of the surface shape recognizing sensor device shown in FIG. 23 will be explained with reference to FIGS. 24A to 24D. The surface of a finger 3 is connected to the ground potential via a resistance Rf of the finger 3. Assume that Rf=0Ω. Accordingly, the potential of the finger surface, i.e., the potential at a node N2 is held at the ground potential (FIG. 24D).

At time t1 in FIG. 24A, the switch SW1 is closed by changing the potential of a control signal P to High level, thereby precharging a potential Vp in the node N1. In this case, the driving voltage Vs of the capacitive element Cs in the signal generating circuit 13 is set at VDD. After that, at time t2 in FIG. 24A, the switch SW is opened by changing the potential of the control signal P to Low level. At the same time, as shown in FIG. 24B, the driving voltage Vs of the capacitive element Cs is decreased by ΔVs from VDD and set at GND, thereby extracting the electric charge from the node N1 to generate a voltage signal to a detection circuit 12.

A change amount ΔV of the voltage signal to be applied to the detection circuit 12 is give by $$\Delta V = \Delta Vs / \{1 + (Cf + Cp)/Cs\} \quad (3)$$

A difference ΔVi between a voltage signal corresponding to a valley of a fingertip skin surface and a voltage signal corresponding to a ridge of a fingertip skin surface is given by $$\Delta Vi = \Delta Vs / \{1 + (Cfv + Cp)/Cs\} - \Delta Vs / \{1 + (Cfr + Cp)/Cs\} \quad (4)$$

Since, therefore, the voltage signal detected by the detection circuit 12 of each sensor cell is a signal reflecting a ridge or valley of a fingerprint, ridges and valleys of a fingertip skin surface can be discriminated by outputs from a plurality of sensor cells.

The surface of the finger 3, however, is connected to the ground potential via the resistance Rf of the finger 3, so no sufficiently large voltage difference ΔVi can be obtained in some cases if the resistance Rf is high because, e.g., the finger 3 is dry. The operation of the surface shape recognizing sensor device when Rf>>0 will be explained with reference to FIGS. 25A to 25D.

The basic operation timings in FIGS. 25A to 25D are the same as in FIGS. 24A to 24D. On a ridge of a fingertip skin surface, however, the potential of the finger surface, i.e., the potential at the node N2 cannot hold the ground potential and fluctuates as shown in FIG. 25D with the potential change at the node N1 shown in FIG. 25C. Consequently, the value of the capacitance Cf formed between the ridge of the fingertip skin surface and the sensor electrode 101 effectively decreases (Cf=αCfr, α<1), and as a result the voltage difference ΔVi (=ΔVs/{1+(Cfv+Cp)/Cs}−ΔVs/{1+(α·Cfr+Cp)/Cs}) decreases as shown in FIG. 25C. This makes it difficult for the surface shape recognizing sensor device shown in FIG. 23 to discriminate between the ridge and valley patterns of a fingerprint image, and as a consequence no clear fingerprint image pattern can be obtained.

DISCLOSURE OF INVENTION

Problem to be Solved by the Invention

As described above, when the conventional surface shape recognizing sensor device is used as a fingerprint sensor for fingerprint authentication, if the resistance Rf of the finger 3 is high, it becomes difficult to discriminate between the ridge and valley patterns of a fingerprint image, so no clear fingerprint image can be obtained any longer. As a consequence, when a fingerprint image deteriorates due to the resistance Rf of the finger 3, the authentication ratio decreases.

The present invention has been made to solve this problem, and has as its object to provide a surface shape recognizing sensor device capable of increasing the sensitivity of detection of a capacitance corresponding to a ridge or valley of the surface of an object to be recognized, e.g., a fingerprint.

Means for Solving the Problem

To achieve the above object, the present invention is characterized by comprising a plurality of sensor cells which are two-dimensionally arranged, detect capacitances corresponding to ridges and valleys of a surface of an object to be recognized, and output signals corresponding to the capacitances, and a signal processor which calculates a surface shape of the object on the basis of the signals input from the sensor cells, the sensor cell comprising a substrate, a first electrode formed on the substrate, a signal output unit which outputs a signal corresponding to a capacitance formed between the first electrode and the surface of the object, a second electrode formed on the substrate so as to be insulated and isolated from the first electrode, and a potential controller which controls a potential of the surface of the object via a capacitance formed between the second electrode and the surface of the object by controlling a potential of the second electrode.

Effects of the Invention

The present invention controls the potential of the surface of an object to be recognized via the capacitance formed between the second electrode and the surface of the object by controlling the potential of the second electrode by using the potential controller. When the resistance of the object is high, therefore, the surface potential of the object can be controlled so as not to fluctuate with the potential change of the first electrode. This makes it possible to increase the sensitivity of detection of the capacitance formed between the first electrode and the surface of the object. As a consequence, ridges and valleys of the surface of the object can be clearly discriminated by outputs from a plurality of sensor cells. Especially when the present invention is used as a fingerprint sensor for fingerprint authentication, it is possible to prevent deterioration of a fingerprint image caused by the surface resistance of the finger, and obtain an effect of preventing a decrease in authentication ratio.

BEST MODE FOR CARRYING OUT THE INVENTION

The principal characteristic feature of a surface shape recognizing sensor device of the present invention is to have a means for increasing the sensitivity of detection of a signal (capacitance) corresponding to a ridge or valley of a surface shape. The differences from the prior art are that each sensor cell of the surface shape recognizing sensor device has a second electrode in addition to a sensor electrode, and the surface potential of a surface shape is controlled by controlling the potential of the second electrode.

Embodiments of the present invention will be described in detail below with reference to the accompanying drawings.

First Embodiment

Figure 1:
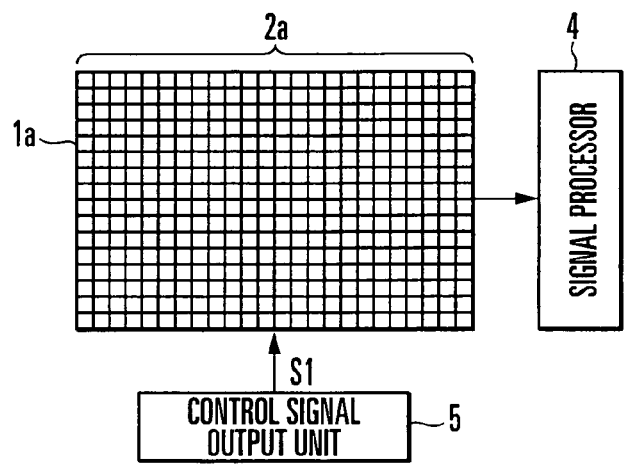
FIG. 1 is a block diagram showing the overall arrangement of a surface shape recognizing sensor device according to the first embodiment of the present invention.

As shown in FIG. 1, a surface shape recognizing sensor device according to the first embodiment of the present invention has a sensor cell array 2a in which a plurality of sensor cells 1a are two-dimensionally arrayed, a signal processor 4, and a control signal output unit 5. Each sensor cell 1a senses a capacitance corresponding to a ridge or valley of the surface of a finger as an object to be recognized, and outputs a signal corresponding to the capacitance to the signal processor 4. The signal processor 4 integrates the input signals from the sensor cells 1a, and calculates the surface shape of the finger. The control signal output unit 5 outputs a control signal S1 to each sensor cell 1a, and controls the operation of the sensor cell 1a.

Figure 2:
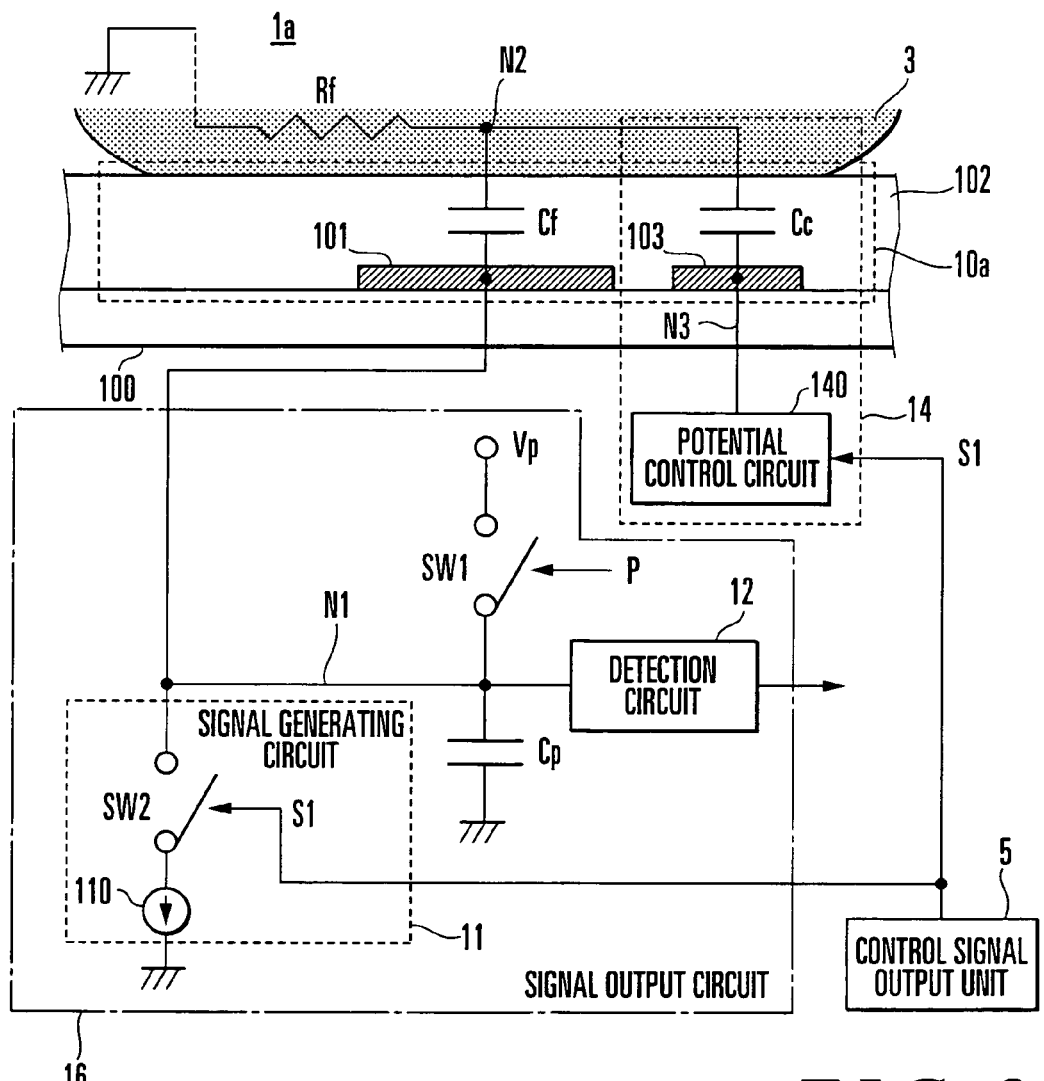
FIG. 2 is a block diagram showing the arrangement of the surface shape recognizing sensor device according to the first embodiment of the present invention.

As shown in FIG. 2, the sensor cell 1a has a detecting element 10a, signal output unit 16, and finger surface potential controller 14.

The detecting element 10a includes an insulating layer 100 on a substrate, a sensor electrode 101 (first electrode) formed on the insulating layer 100, a high-sensitivity electrode 103 (second electrode, control electrode) formed on the insulating layer 100 so as to be insulated and isolated from the sensor electrode 101, and a passivation film 102 so formed as to cover the sensor electrode 101 and high-sensitivity electrode 103. The surface of the passivation film 102 is planarized.

The signal output unit 16 outputs, as the output from the sensor cell 1a, a signal corresponding to a capacitance Cf formed between the sensor electrode 101 and the skin of a finger 3 in contact with the passivation film 102, and more specifically includes a switch SW1 (charging circuit), signal generating circuit 11, and detection circuit 12. The switch SW1 applies a potential Vp to a node N1 as a connecting point between the sensor electrode 101 of the detecting element 10a and the output terminal of the signal generating circuit 11, thereby storing an electric charge. The signal generating circuit 11 generates a voltage signal corresponding to the capacitance Cf formed between the skin of the finger 3 and the sensor electrode 101. The signal generating circuit 11 includes a first current source 110 for removing the electric charge from the node N1, and a switch SW2 (first switching element) which is placed between the current source 110 and the node N1 and generates the voltage signal by electrically connecting the current source 110 and node N1 for only a predetermined time after the electric charge is stored in the node N1. The detection circuit 12 detects the voltage signal from the signal generating circuit 11 after the electric charge is stored in the node N1, and outputs the signal as the output from the signal output unit 16.

The finger surface potential controller 14 has a potential control circuit 140 which controls the potential of the high-sensitivity electrode 103. The switch SW2 of the signal generating circuit 11 and the potential control circuit 140 are together controlled by the control signal S1 input from the control signal output circuit 5. Note that Cp in FIG. 2 denotes a parasitic capacitance.

Figure 20:
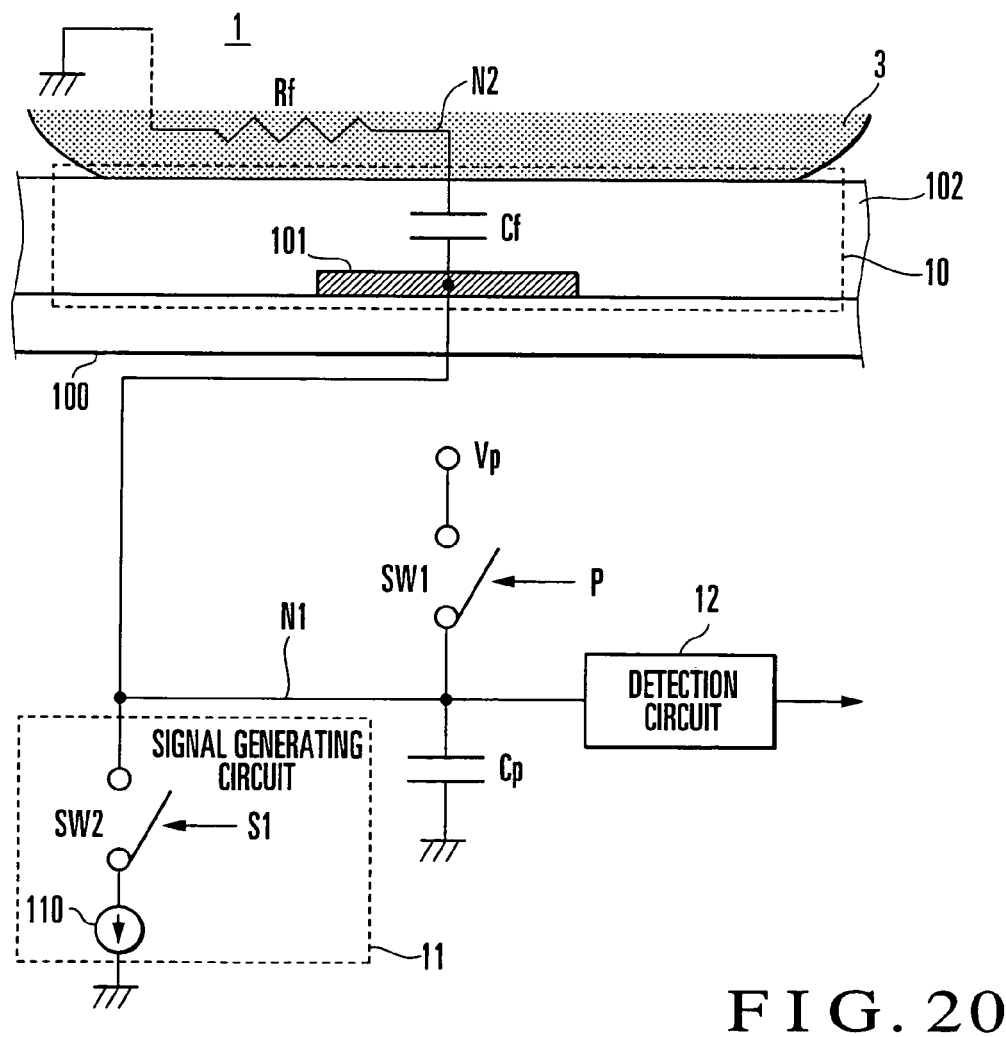
FIG. 20 is a block diagram showing the arrangement of a surface shape recognizing sensor device as the first prior art.

The surface shape recognizing sensor device shown in FIG. 2 aims at solving the problem of the conventional surface shape recognizing sensor device shown in FIG. 20, and is obtained by adding the high-sensitivity electrode 103 and potential control circuit 140 to the conventional surface shape recognizing sensor device. Since the potential control circuit 140 controls the potential of the surface (a node N2) of the finger 3 via a capacitance Cc formed between the surface of the finger 3 and the high-sensitivity electrode 103, the potential at the node N2 can be controlled when a resistance Rf is high because, e.g., the finger 3 is dry, thereby increasing the sensitivity of detection of the capacitance Cf.

Figure 3A:
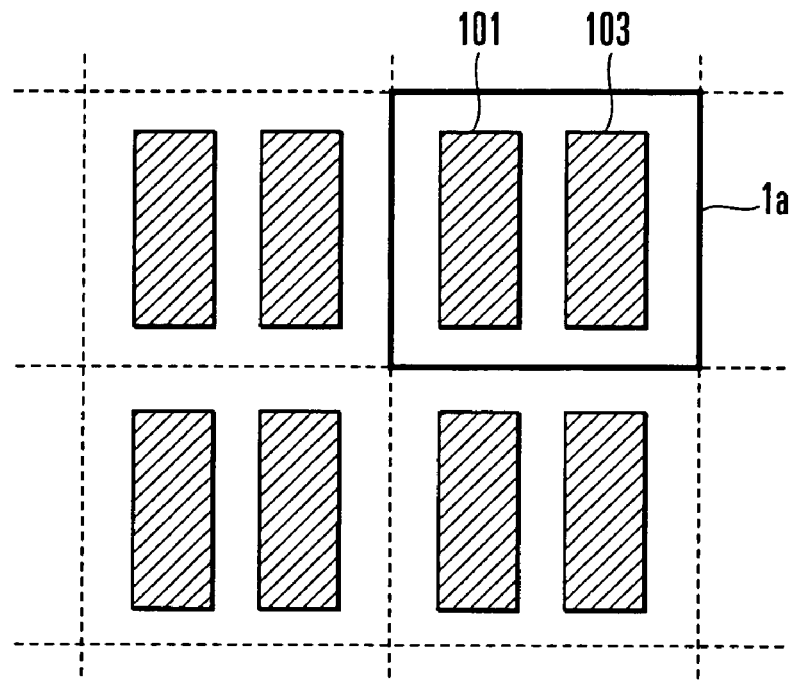
FIG. 3A is a plan view showing an example of the layout pattern of sensor electrodes and high-sensitivity electrodes in a sensor cell array of the surface shape recognizing sensor device shown in FIG. 1.
Figure 3B:
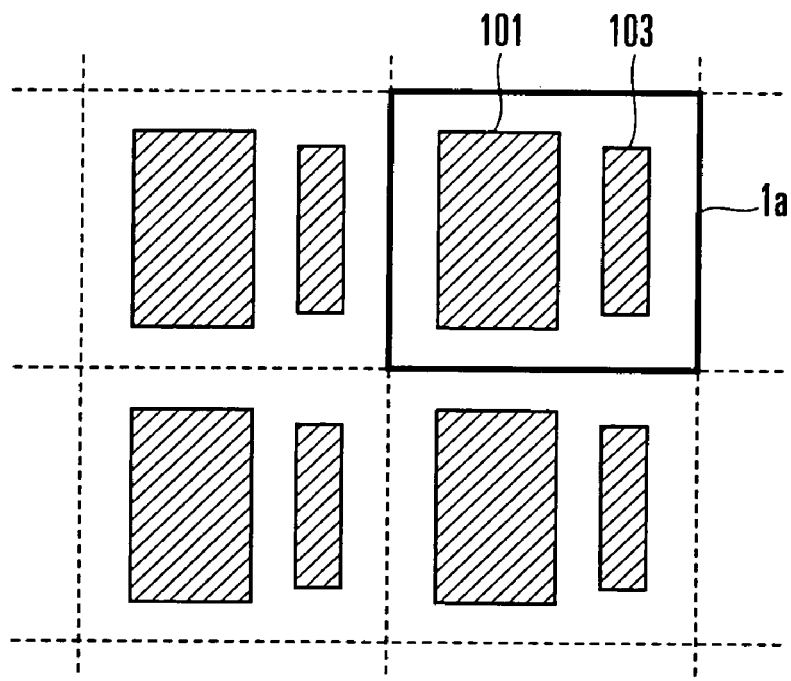
FIG. 3B is a plan view showing another example of the layout pattern of the sensor electrodes and high-sensitivity electrodes in the sensor cell array of the surface shape recognizing sensor device shown in FIG. 1.

As shown in FIGS. 3A and 3B, each sensor cell 1a of the sensor cell array 2a incorporates the sensor electrode 101 and high-sensitivity electrode 103. The larger the area of the high-sensitivity electrode 103, the more easily the potential of the finger 3 is controlled. However, to increase the detection sensitivity by arranging both the sensor electrode 101 and high-sensitivity electrode 103 in the limited region of the sensor cell 1a, it is desirable to make the area of the high-sensitivity electrode 103 equal to that of the sensor electrode 101 as shown in FIG. 3A, or make the area of the high-sensitivity electrode 103 smaller than that of the sensor electrode 101 as shown in FIG. 3B.

An example of the operation of the surface shape recognizing sensor device shown in FIG. 1 when Rf>>0 will be explained below with reference to FIGS. 4A to 4E.

Figure 4A:
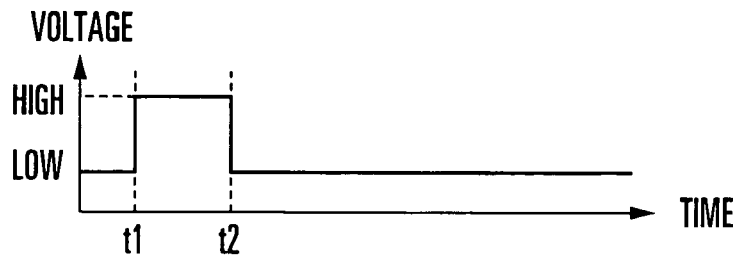
FIG. 4A is one of timing charts for explaining an example of the operation of the surface shape recognizing sensor device shown in FIG. 1 when the resistance of a finger is high, in which the change in control signal P with time is shown.
Figure 4B:
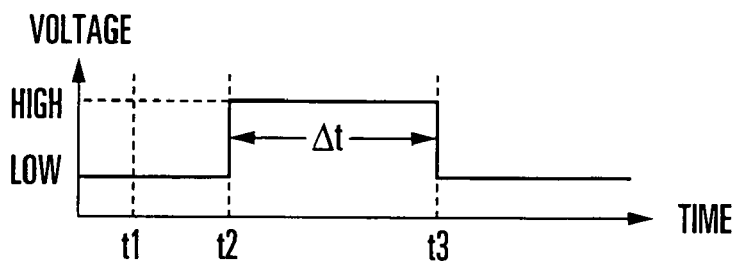
FIG. 4B is one of the timing charts for explaining the example of the operation of the surface shape recognizing sensor device shown in FIG. 1 when the resistance of a finger is high, in which the change in control signal S1 with time is shown.

Initially, a control signal P for controlling opening/closure of the switch SW1 is Low level (FIG. 4A). The control signal S1 for controlling opening/closure of the switch SW2 is also Low level (FIG. 4B). Accordingly, both the switches SW1 and SW2 are open. In this case, the potential at the node N1 is lower than the potential Vp (FIG. 4C).

Figure 4C:
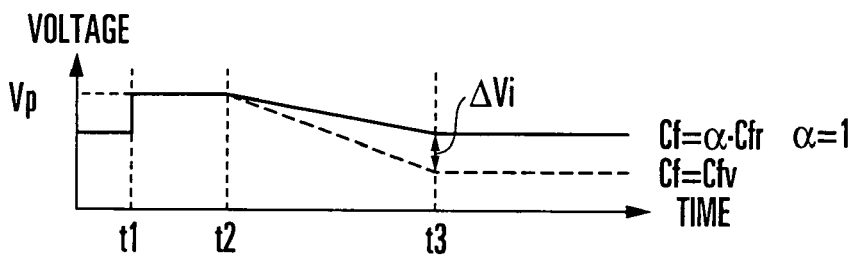
FIG. 4C is one of the timing charts for explaining the example of the operation of the surface shape recognizing sensor device shown in FIG. 1 when the resistance of a finger is high, in which the change in potential at a node N1 is shown.

In this state, when the control signal P changes from Low level to High level at time t1 in FIG. 4A, the switch SW1 is closed and turned on, and as a consequence the potential at the node N1 is precharged to the potential Vp (FIG. 4C).

After the precharge is completed, the control signal P changes to Low level at time t2 in FIG. 4A, and simultaneously the control signal S1 changes to High level as shown in FIG. 4B. Accordingly, the switch SW1 is turned off, the switch SW2 is turned on, and the electric charge stored in the node N1 is extracted by the current source 110. As a consequence, the potential (voltage signal) at the node N1 decreases (FIG. 4C). The control signal S1 maintains High level for a predetermined period Δt. A potential drop ΔV at the node N1 from the potential Vp when Δt has elapsed is given by equation (1) presented earlier where I is the current value of the current source 110 and Cp is a parasitic capacitance.

Figure 4D:
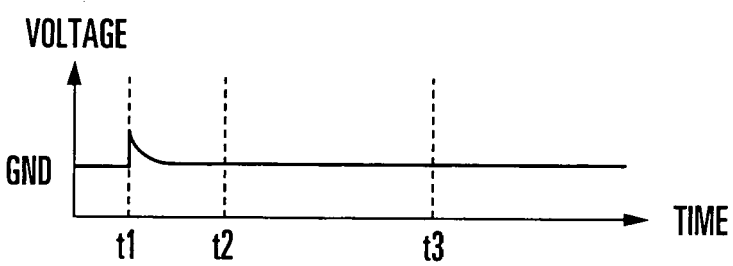
FIG. 4D is one of the timing charts for explaining the example of the operation of the surface shape recognizing sensor device shown in FIG. 1 when the resistance of a finger is high, in which the change in potential at a node N2 is shown.
Figure 4E:
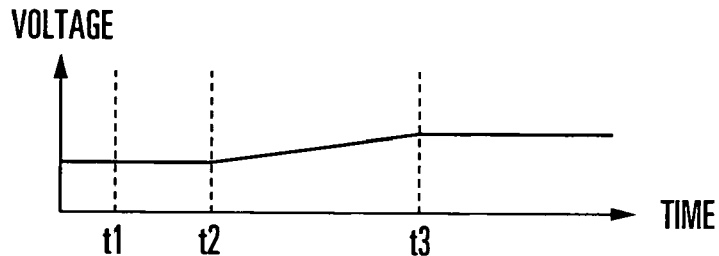
FIG. 4E is one of the timing charts for explaining the example of the operation of the surface shape recognizing sensor device shown in FIG. 1 when the resistance of a finger is high, in which the change in potential at a node N3 is shown.
Figure 21A:
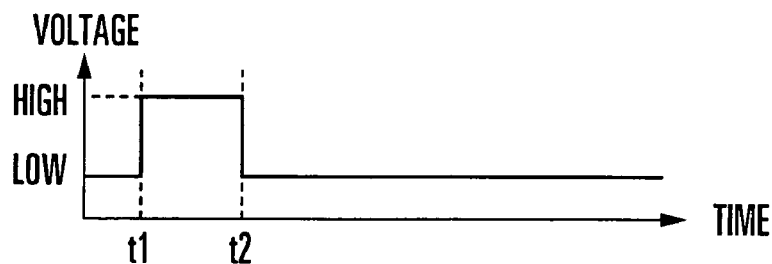
FIG. 21A is one of timing charts for explaining a normal operation of the surface shape recognizing sensor device shown in FIG. 20, in which the change in control signal P with time is shown.
Figure 21B:
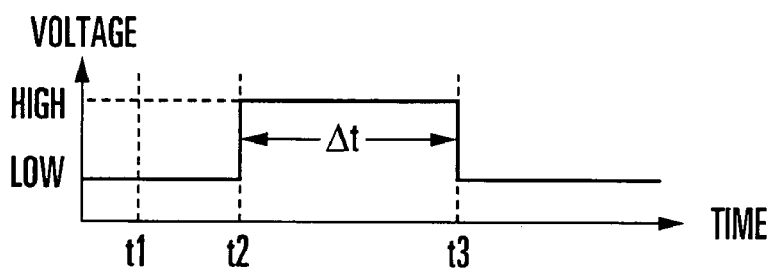
FIG. 21B is one of the timing charts for explaining the normal operation of the surface shape recognizing sensor device shown in FIG. 20, in which the change in control signal S1 with time is shown.
Figure 21C:
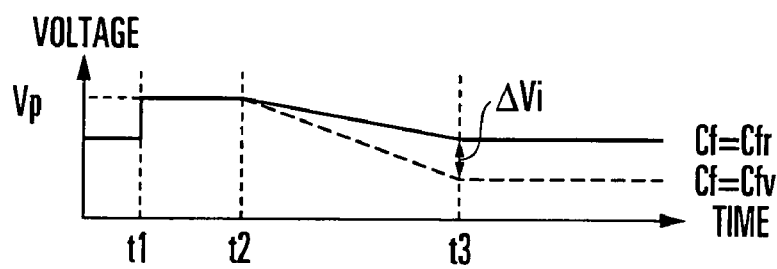
FIG. 21C is one of the timing charts for explaining the normal operation of the surface shape recognizing sensor device shown in FIG. 20, in which the change in potential at a node N1 is shown.
Figure 21D:
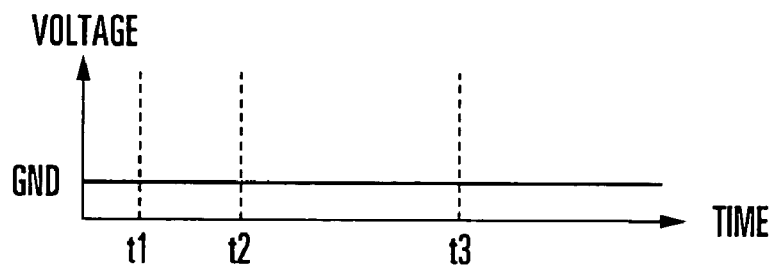
FIG. 21D is one of the timing charts for explaining the normal operation of the surface shape recognizing sensor device shown in FIG. 20, in which the change in potential at a node N2 is shown.
Figure 22A:
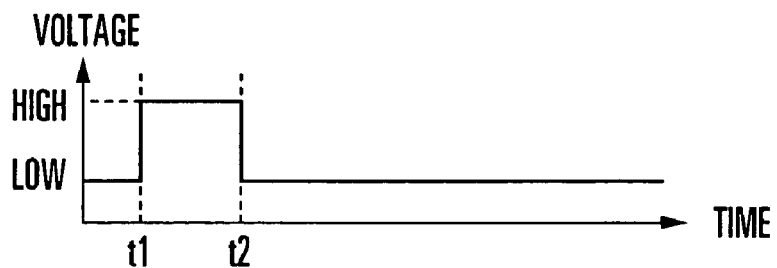
FIG. 22A is one of timing charts for explaining the operation of the surface shape recognizing sensor device shown in FIG. 20 when the resistance of a finger is high, in which the change in control signal P with time is shown.
Figure 22B:
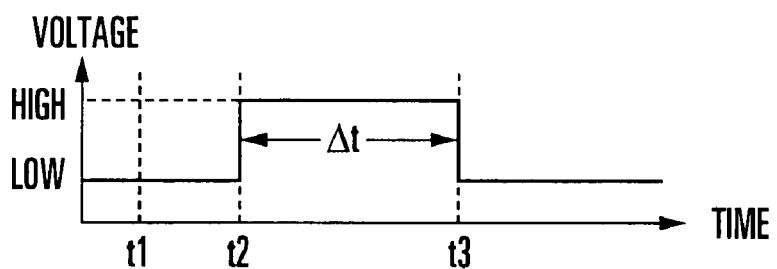
FIG. 22B is one of the timing charts for explaining the operation of the surface shape recognizing sensor device shown in FIG. 20 when the resistance of a finger is high, in which the change in control signal S1 with time is shown.
Figure 22C:
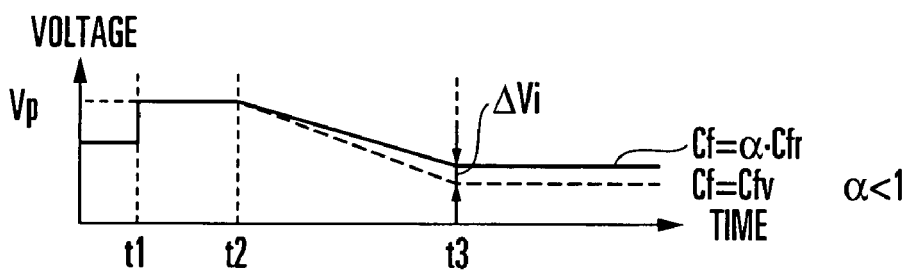
FIG. 22C is one of the timing charts for explaining the operation of the surface shape recognizing sensor device shown in FIG. 20 when the resistance of a finger is high, in which the change in potential at the node N1 is shown.
Figure 22D:
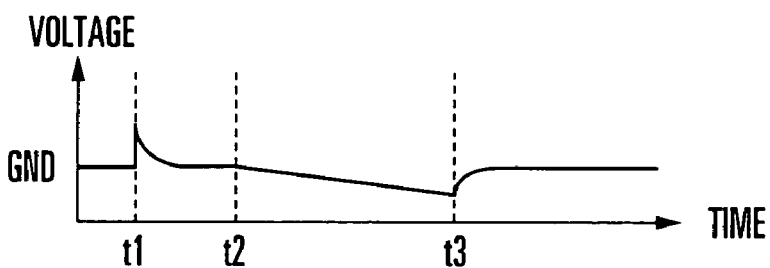
FIG. 22D is one of the timing charts for explaining the operation of the surface shape recognizing sensor device shown in FIG. 20 when the resistance of a finger is high, in which the change in potential at the node N2 is shown.

In the surface shape recognizing sensor device shown in FIG. 1, unlike in FIG. 22, the potential at a node N3 as a connecting point between the output of the potential control circuit 140 and the high-sensitivity electrode 103 is changed in the opposite direction to the potential change at the node N1 during a period from time t2 to time t3 as shown in FIG. 4E. More specifically, the potential at the node N3 is raised. When a ridge of the fingerprint faces the sensor cell 1a, the capacitance Cc formed between the high-sensitivity electrode 103 and the surface of the finger 3 is large. For this reason, the potential at the node N2 can be controlled via the capacitance Cc by controlling the potential at the node N3. By thus controlling the potential at the node N3, therefore, the potential fluctuation at the node N2 during the period from time t2 to time 3 can be suppressed as shown in FIG. 4D. This makes it possible to prevent the value of the capacitance Cf from effectively decreasing, and obtain α=1 when Cf=α·Cfr. Note that when a valley of the fingertip skin surface faces the sensor cell 1a, the capacitance Cc formed between the high-sensitivity electrode 103 and the surface of the finger 3 is small, so the potential at the node N2 is not influenced. Consequently, as shown in FIG. 4C, the magnitude of a difference ΔVi between a voltage signal corresponding to a valley of the fingertip skin surface and a voltage signal corresponding to a ridge of the fingertip skin surface can be made equal to that shown in FIG. 21C, i.e., that when the resistance Rf of the finger 3 is 0Ω.

Figure 5:
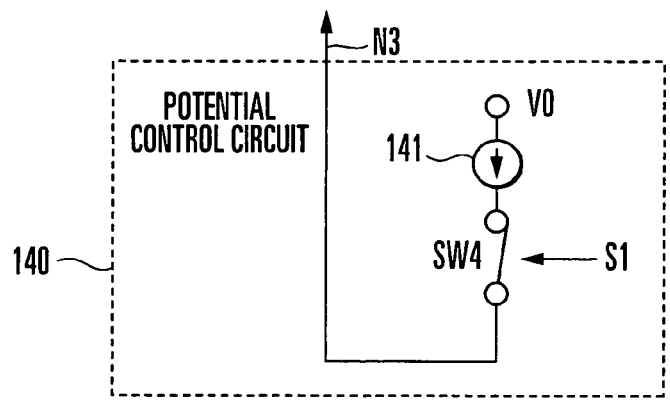
FIG. 5 is a block diagram showing an implementation example of a potential control circuit of the first embodiment of the present invention.

As shown in FIG. 5, for example, the potential control circuit 140 includes a second current source 141 for storing an electric charge in the node N3, and a switch SW4 (second switching element) placed between the node N3 and the current source 141. During a period in which the switch SW4 is turned on, the current source 141 stores an electric charge in the node N3, so the potential at the node N3 rises. The control signal S1 used in the signal generating circuit 11 is also used as a control signal of the switch SW4, so both the switches SW2 and SW4 are turned on when the control signal S1 is High level. The increase in number of control signals can be prevented by using the control signal S1 for both the switches SW2 and SW4.

Another example of the operation of the surface shape recognizing sensor device shown in FIG. 1 when Rf>>0 will be explained below with reference to FIGS. 6A to 6E.

Figure 6A:
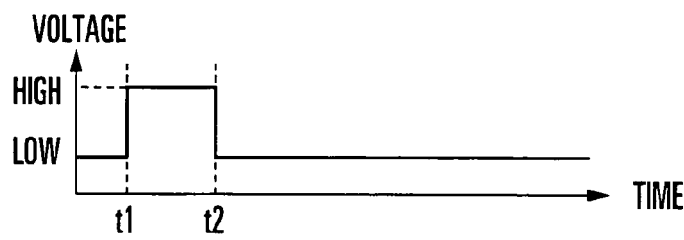
FIG. 6A is one of timing charts for explaining an example of the operation of the surface shape recognizing sensor device shown in FIG. 1 when the resistance of a finger is high, in which the change in control signal P with time is shown.
Figure 6B:
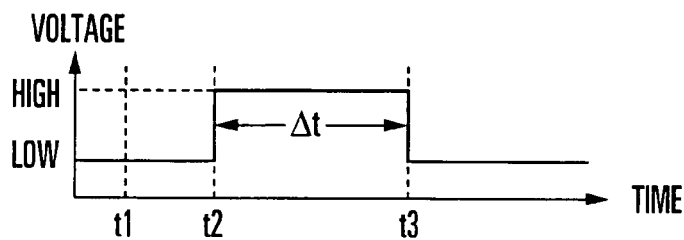
FIG. 6B is one of the timing charts for explaining the example of the operation of the surface shape recognizing sensor device shown in FIG. 1 when the resistance of a finger is high, in which the change in control signal S1 with time is shown.
Figure 6C:
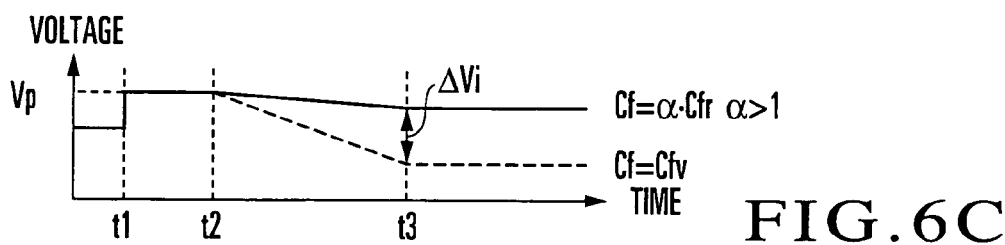
FIG. 6C is one of the timing charts for explaining the example of the operation of the surface shape recognizing sensor device shown in FIG. 1 when the resistance of a finger is high, in which the change in potential at the node N1 is shown.
Figure 6D:
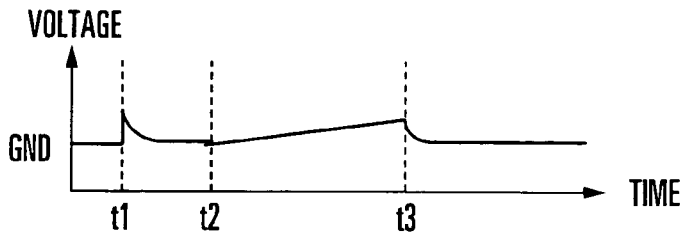
FIG. 6D is one of the timing charts for explaining the example of the operation of the surface shape recognizing sensor device shown in FIG. 1 when the resistance of a finger is high, in which the change in potential at the node N2 is shown.
Figure 6E:
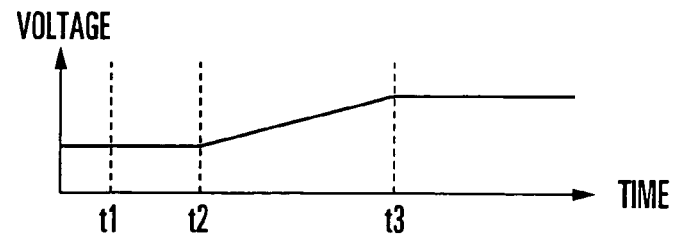
FIG. 6E is one of the timing charts for explaining the example of the operation of the surface shape recognizing sensor device shown in FIG. 1 when the resistance of a finger is high, in which the change in potential at the node N3 is shown.

The basic operation is the same as the operation shown in FIGS. 4A to 4E. The differences from FIGS. 4A to 4E are that, as shown in FIG. 6E, the potential change at the node N3 is larger than that shown in FIG. 4E, and, as shown in FIG. 6D, the potential at the node N2 changes in a direction to increase during the period from time t2 to time t3. This makes it possible to effectively increase the value of the capacitance Cf, and obtain α>1 when Cf=α·Cfr. Consequently, as shown in FIG. 6C, the magnitude of the difference ΔVi between the voltage signal corresponding to a valley of the fingertip skin surface and the voltage signal corresponding to a ridge of the fingertip skin surface can be made larger than that shown in FIG. 21C. Since, therefore, it is readily possible to determine whether the voltage signal detected by the detection circuit 12 of each sensor cell corresponds to a ridge or valley of the fingertip skin surface, ridges and valleys of the fingertip skin surface can be clearly discriminated by outputs from a plurality of sensor cells.

In this embodiment as explained above, the potential control circuit 140 controls the potential of the surface (node N2) of the finger 3 via the capacitance Cc formed between the surface of the finger 3 and the high-sensitivity electrode 103, so it is possible to control the potential at the node N2 when the resistance Rf of the finger 3 is high, and increase the sensitivity of detection of the capacitance Cf.

Note that although the potential at the node N3 is changed in accordance with the control signal S1 in this embodiment, what is important is to change the potential at the node N3 in the opposite direction to the potential change at the node N1, so the method is not limited to the use of the control signal S1, and the timing at which the potential at the node N3 is changed is not limited to the period from time t2 to time t3.

Note also that in this embodiment, a signal obtained by storing an electric charge in the node N1 and then removing this electric charge for only a predetermined time is used as the output signal from the sensor cell 1a. However, it is also possible to use, as the output from the sensor cell 1a, a signal obtained by removing the electric charge from the node N1 and then storing an electric charge in the node N1 for only a predetermined time. In this case, the potential Vp shown in FIG. 2 is set at the ground potential to allow the switch SW1 to function as a discharging circuit, and the current source 110 is connected in the opposite direction to that shown in FIG. 2 so that an electric charge can be stored in the node N1. In this arrangement, if the resistance Rf is high because, e.g., the finger 3 is dry, the potential at the node N2 rises in accordance with the potential change at the node N1 when an electric charge is stored in the node N1. To prevent this, the potential control circuit 140 changes the potential at the node N3 in the opposite direction to the potential change at the node N1. That is, the potential at the node N3 is decreased. More specifically, the current source 141 is connected in the opposite direction to that shown in FIG. 5 so that the potential control circuit 140 can remove the electric charge from the node N3.

Second Embodiment

The second embodiment of the present invention will be described below.

Figure 7:
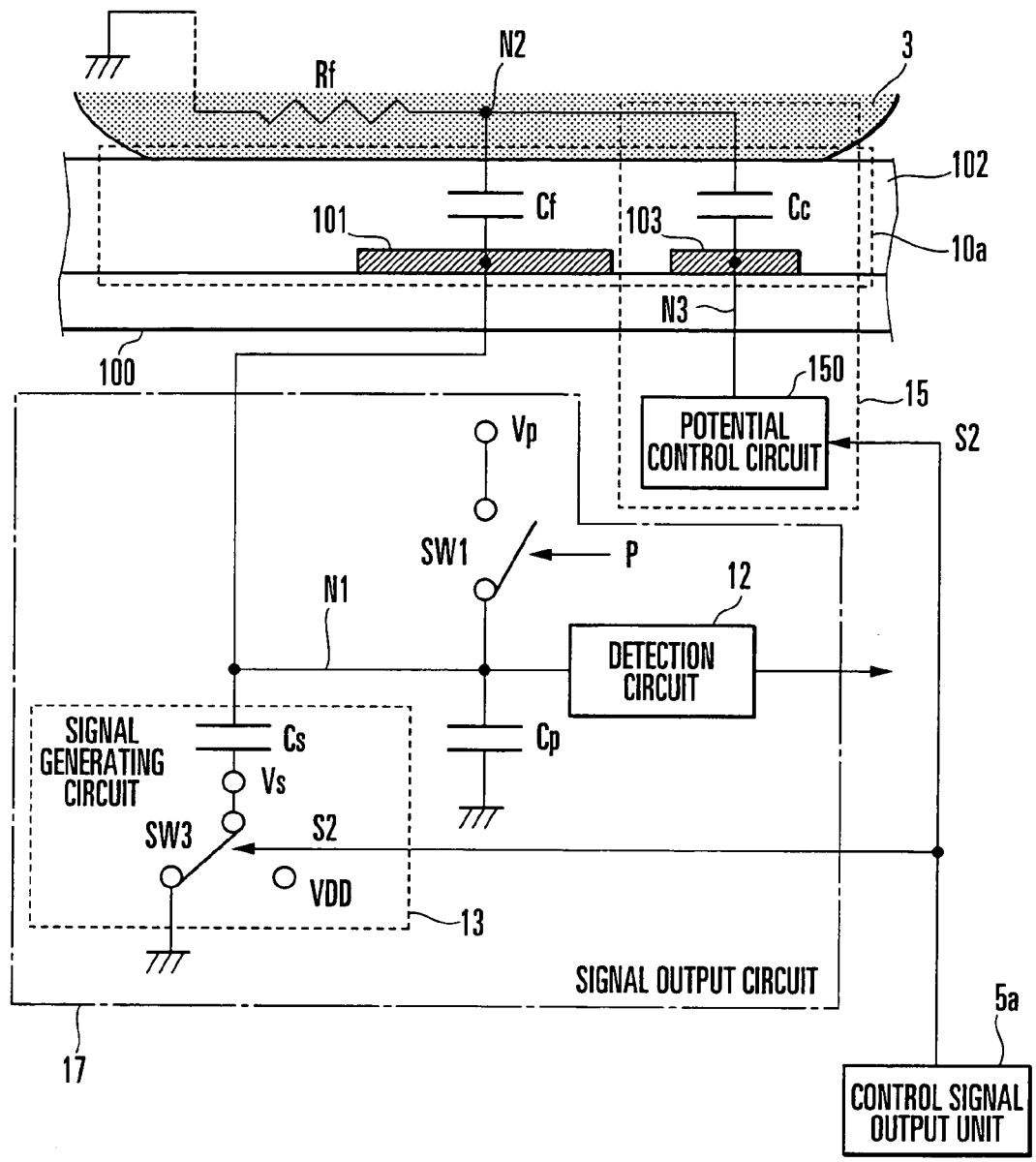
FIG. 7 is a block diagram showing the arrangement of a surface shape recognizing sensor device according to the second embodiment of the present invention.

A surface shape recognizing sensor device according to the second embodiment of the present invention has a sensor cell array in which a plurality of sensor cells are two-dimensionally arranged, and each sensor cell has a detecting element 10a, signal output unit 17, and finger surface potential controller 15 as shown in FIG. 7. Note that the same reference numerals as in FIG. 2 denote the same parts in FIG. 7.

Similar to FIG. 1, the detecting element 10a includes an insulating layer 100 on a substrate, a sensor electrode 101, a high-sensitivity electrode 103, and a passivation film 102.

The signal output unit 17 outputs, as the output from a sensor cell 1a, a signal corresponding to a capacitance Cf formed between the sensor electrode 101 and the skin of a finger 3 in contact with the passivation film 102, and more specifically includes a switch SW1 (charging circuit), signal generating circuit 13, and detection circuit 12. The switch SW1 applies a potential Vp to a node N1 as a connecting point between the sensor electrode 101 of the detecting element 10a and the output terminal of the signal generating circuit 13, thereby storing an electric charge. The signal generating circuit 13 generates a voltage signal corresponding to the capacitance Cf formed between the skin of the finger 3 and the sensor electrode 101. The signal generating circuit 13 includes a switch SW3 (third switching element) which selects and outputs one of a power supply potential VDD (first potential) and a ground potential GND (second potential) lower than VDD, and a capacitive element Cs formed between the output terminal of the switch SW3 and the node N1. The detection circuit 12 detects the voltage signal from the signal generating circuit 13, and outputs the signal as the output from the signal output unit 17.

The finger surface potential controller 15 has a potential control circuit 150 which controls the potential of the high-sensitivity electrode 103. The switch SW3 of the signal generating circuit 13 and the potential control circuit 150 are together controlled by a control signal S2 input from a control signal output circuit 5a. Note that Cp in FIG. 7 denotes a parasitic capacitance.

Figure 23:
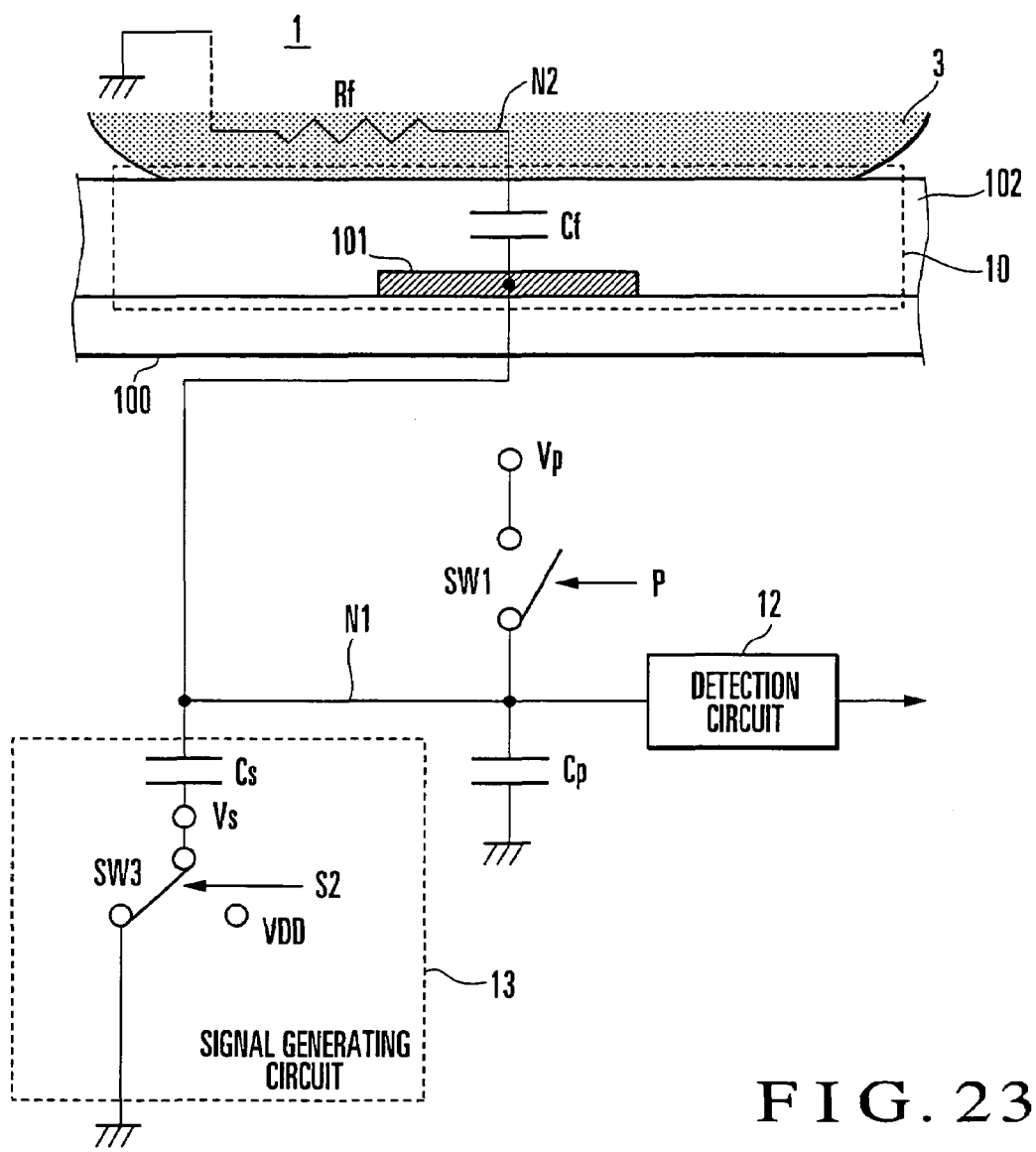
FIG. 23 is a block diagram showing the arrangement of a surface shape recognizing sensor device as the second prior art.

The surface shape recognizing sensor device shown in FIG. 7 aims at solving the problem of the conventional surface shape recognizing sensor device shown in FIG. 23, and is obtained by adding the high-sensitivity electrode 103 and potential control circuit 150 to the conventional surface shape recognizing sensor device. Since the potential control circuit 150 controls the potential of the surface (a node N2) of the finger 3 via a capacitance Cc formed between the surface of the finger 3 and the high-sensitivity electrode 103, the potential at the node N2 can be controlled when a resistance Rf of the finger 3 is high because, e.g., the finger 3 is dry, thereby increasing the sensitivity of detection of the capacitance Cf.

An example of the operation of the surface shape recognizing sensor device shown in FIG. 7 when Rf>>0 will be explained below with reference to FIGS. 8A to 8E.

Figure 8A:
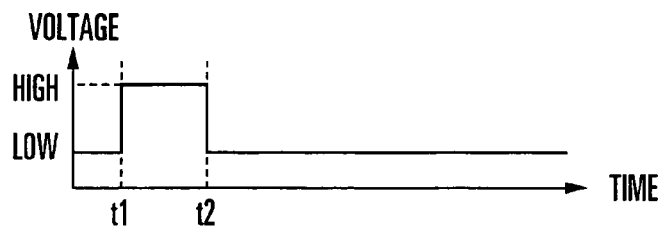
FIG. 8A is one of timing charts for explaining an example of the operation of the surface shape recognizing sensor device shown in FIG. 7 when the resistance of a finger is high, in which the change in control signal P with time is shown.
Figure 8B:
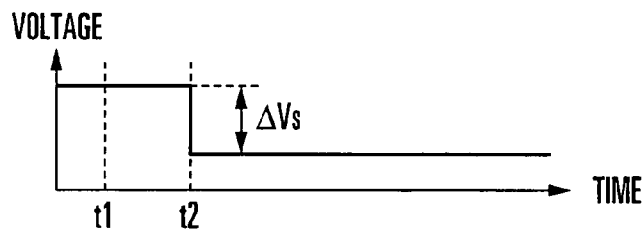
FIG. 8B is one of the timing charts for explaining the example of the operation of the surface shape recognizing sensor device shown in FIG. 7 when the resistance of a finger is high, in which the change in driving voltage Vs of a capacitive element Cs with time is shown.

At time t1 in FIG. 8A, the potential of a control signal P is changed to High level to close the switch SW1, thereby precharging the potential Vp in the node N1. On the other hand, during a period before time t2, the control signal S2 causes the switch SW3 to select the power supply potential VDD, thereby setting a driving voltage Vs of the capacitive element Cs at the power supply potential VDD (FIG. 8B). After that, at time t2 in FIG. 8A, the potential of the control signal P is changed to Low level to open the switch SW1, and simultaneously the control signal S2 causes the switch SW3 to select the ground potential GND, thereby lowering the driving voltage Vs of the capacitive element Cs by ΔVs to generate a voltage signal to the detection circuit 12.

Figure 8C:
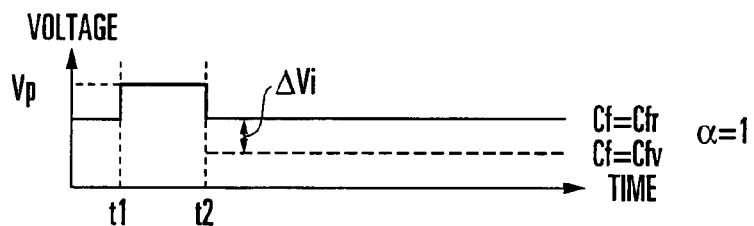
FIG. 8C is one of the timing charts for explaining the example of the operation of the surface shape recognizing sensor device shown in FIG. 7 when the resistance of a finger is high, in which the change in potential at a node N1 is shown.
Figure 8D:
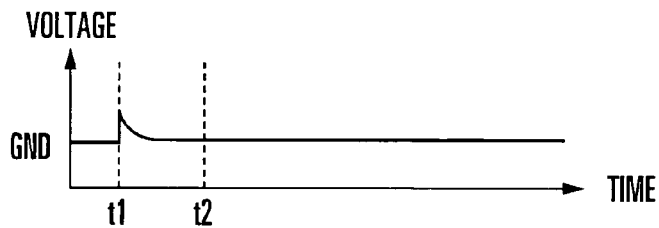
FIG. 8D is one of the timing charts for explaining the example of the operation of the surface shape recognizing sensor device shown in FIG. 7 when the resistance of a finger is high, in which the change in potential at a node N2 is shown.
Figure 8E:
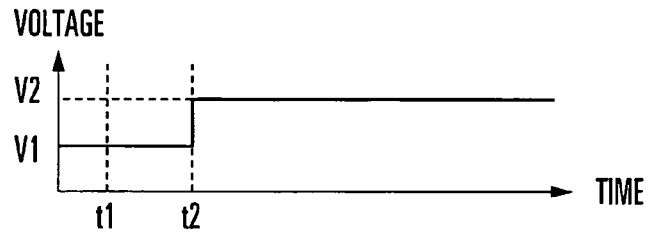
FIG. 8E is one of the timing charts for explaining the example of the operation of the surface shape recognizing sensor device shown in FIG. 7 when the resistance of a finger is high, in which the change in potential at a node N3 is shown.
Figure 24A:
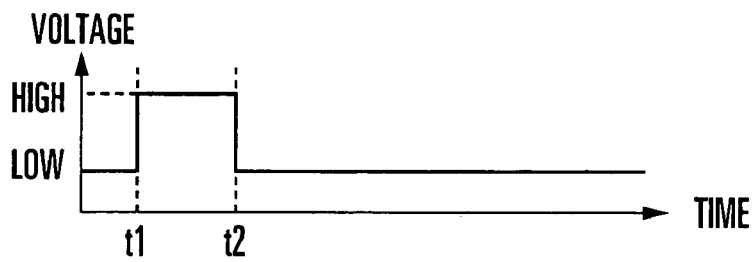
FIG. 24A is one of timing charts for explaining a normal operation of the surface shape recognizing sensor device shown in FIG. 23, in which the change in control signal P with time is shown.
Figure 24B:
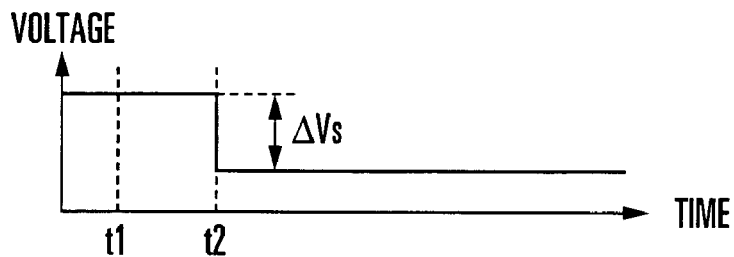
FIG. 24B is one of the timing charts for explaining the normal operation of the surface shape recognizing sensor device shown in FIG. 23, in which the change in driving voltage Vs of a capacitive element Cs with time is shown.
Figure 24C:
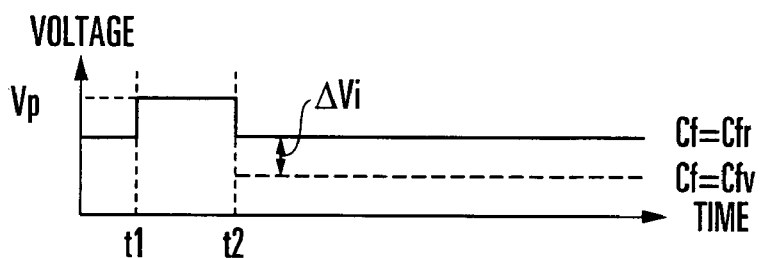
FIG. 24C is one of the timing charts for explaining the normal operation of the surface shape recognizing sensor device shown in FIG. 23, in which the change in potential at a node N1 is shown.
Figure 24D:
FIG. 24D is one of the timing charts for explaining the normal operation of the surface shape recognizing sensor device shown in FIG. 23, in which the change in potential at a node N2 is shown.
Figure 25A:
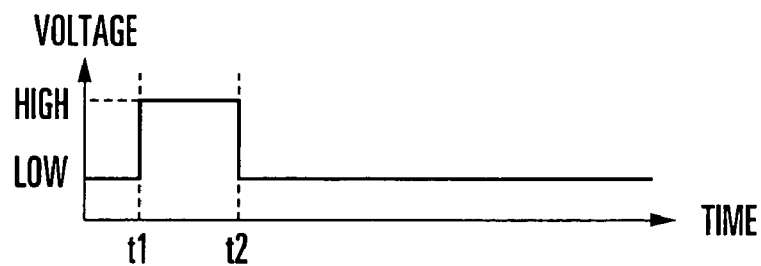
FIG. 25A is one of timing charts for explaining the operation of the surface shape recognizing sensor device shown in FIG. 23 when the resistance of a finger is high, in which the change in control signal P with time is shown.
Figure 25B:
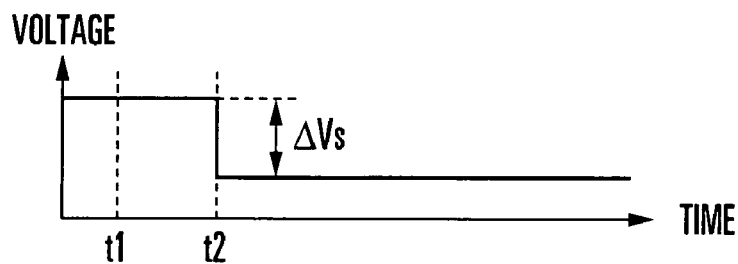
FIG. 25B is one of the timing charts for explaining the operation of the surface shape recognizing sensor device shown in FIG. 23 when the resistance of a finger is high, in which the change in driving voltage Vs of the capacitive element Cs with time is shown.
Figure 25C:
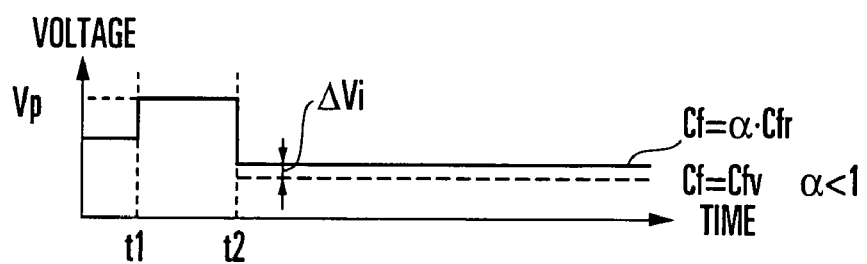
FIG. 25C is one of the timing charts for explaining the operation of the surface shape recognizing sensor device shown in FIG. 23 when the resistance of a finger is high, in which the change in potential at the node Ni is shown.
Figure 25D:
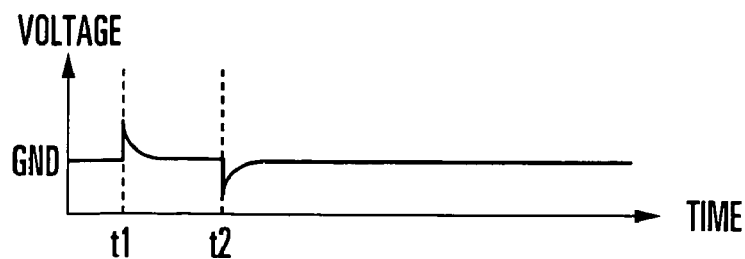
FIG. 25D is one of the timing charts for explaining the operation of the surface shape recognizing sensor device shown in FIG. 23 when the resistance of a finger is high, in which the change in potential at the node N2 is shown.

In the surface shape recognizing sensor device shown in FIG. 7, unlike in FIG. 25, the potential at a node N3 as the output of the potential control circuit 150 is changed in the opposite direction to the potential change at the node N1 during a period after time t2 as shown in FIG. 8E, so the potential fluctuation at the node N2 after time t2 can be suppressed as shown in FIG. 8D. This makes it possible to prevent the value of the capacitance Cf from effectively decreasing, and obtain α=1 when Cf=α·Cfr. Consequently, as shown in FIG. 8C, the magnitude of a difference ΔVi between a voltage signal corresponding to a valley of the finger print and a voltage signal corresponding to a ridge of the fingerprint can be made equal to that shown in FIG. 24C, i.e., that when the resistance Rf of the finger 3 is 0Ω.

Figure 9A:
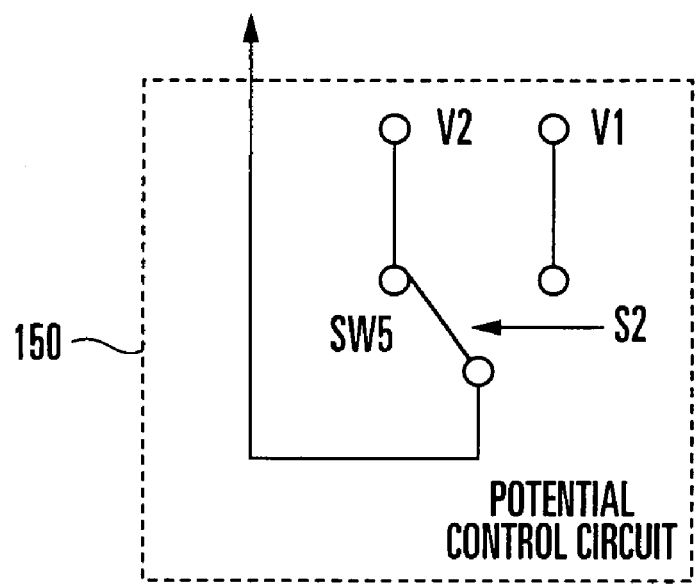
FIG. 9A is a block diagram showing an implementation example of a potential control circuit of the second embodiment of the present invention.

As shown in FIG. 9A, for example, the potential control circuit 150 includes a switch SW5 (setting unit) which selects a predetermined potential V1 (third potential) or V2 (fourth potential) and outputs the selected potential to the high-sensitivity electrode 103. The control signal S2 used in the signal generating circuit 13 is also used as a control signal of the switch SW5, and the control signal S2 causes the switch SW5 to select the potential V1 during the period before time t2 in FIG. 8E, and select the potential V2 (V1<V2) at time t2. The increase in number of control signals can be prevented by using the control signal S2 for both the switches SW3 and SW5.

Figure 9B:
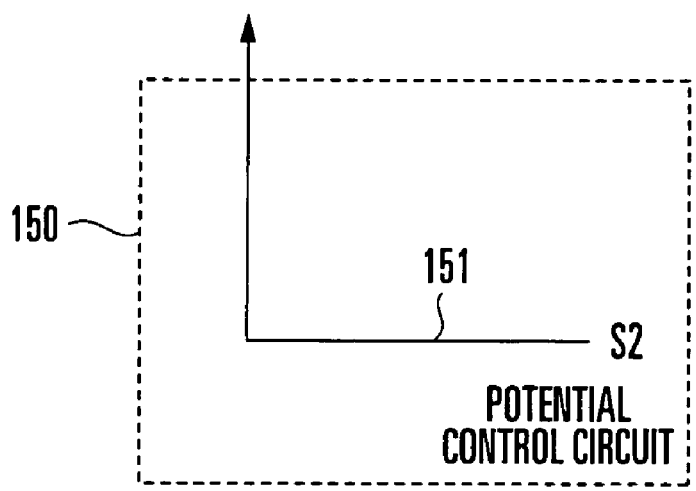
FIG. 9B is a block diagram showing another implementation example of the potential control circuit of the second embodiment of the present invention.

As shown in FIG. 9B, for example, the potential control circuit 150 may also be formed by a signal line 151 (setting unit) which supplies the control signal S2 to the high-sensitivity electrode 103. Since the potential of the control signal S2 is directly used, the potential control circuit 150 can be implemented without using any additional circuit. In this arrangement, the control signal S2 has the same waveform as the potential at the node N3 shown in FIG. 8E.

Another example of the operation of the surface shape recognizing sensor device shown in FIG. 7 when Rf>>0 will be explained below with reference to FIGS. 10A to 10E.

Figure 10A:
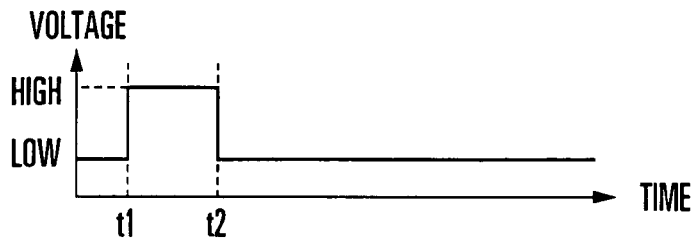
FIG. 10A is one of timing charts for explaining another example of the operation of the surface shape recognizing sensor device shown in FIG. 7 when the resistance of a finger is high, in which the change in control signal P with time is shown.
Figure 10B:
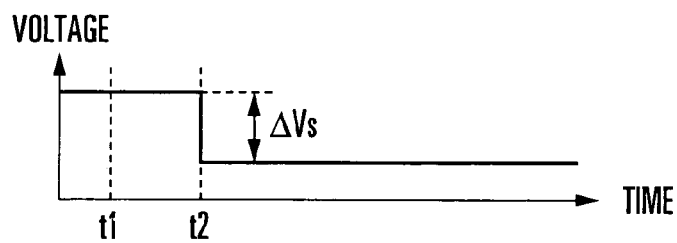
FIG. 10B is one of the timing charts for explaining the other example of the operation of the surface shape recognizing sensor device shown in FIG. 7 when the resistance of a finger is high, in which the change in driving voltage Vs of the capacitive element Cs with time is shown.
Figure 10C:
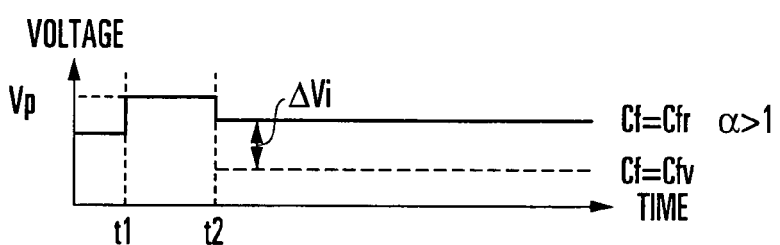
FIG. 10C is one of the timing charts for explaining the other example of the operation of the surface shape recognizing sensor device shown in FIG. 7 when the resistance of a finger is high, in which the change in potential at the node N1 is shown.
Figure 10D:
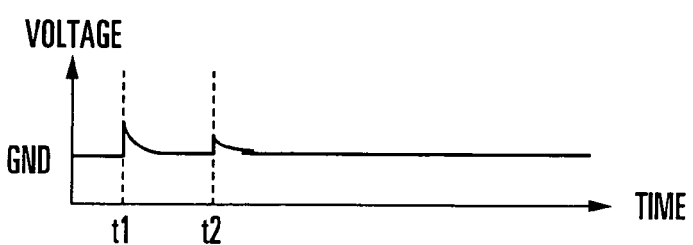
FIG. 10D is one of the timing charts for explaining the other example of the operation of the surface shape recognizing sensor device shown in FIG. 7 when the resistance of a finger is high, in which the change in potential at the node N2 is shown.
Figure 10E:
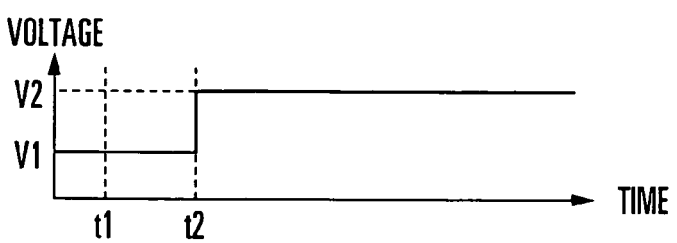
FIG. 10E is one of the timing charts for explaining the other example of the operation of the surface shape recognizing sensor device shown in FIG. 7 when the resistance of a finger is high, in which the change in potential at the node N3 is shown.

The basic operation is the same as the operation shown in FIGS. 8A to 8E. The differences from FIGS. 8A to 8E are that, as shown in FIG. 10E, the potential change at the node N3 is larger than that shown in FIG. 8E, and, as shown in FIG. 10D, the potential at the node N2 transiently changes in a direction to increase at the timing of time t2. This makes it possible to effectively increase the value of the capacitance Cf, and obtain α>1 when Cf=α·Cfr. Consequently, as shown in FIG. 10C, the magnitude of the difference ΔVi between the voltage signal corresponding to a valley of the fingertip skin surface and the voltage signal corresponding to a ridge of the fingertip skin surface can be made larger than that shown in FIG. 24C. Since, therefore, it is readily possible to determine whether the voltage signal detected by the detection circuit 12 of each sensor cell corresponds to a ridge or valley of the fingertip skin surface, ridges and valleys of the fingertip skin surface can be clearly discriminated by outputs from a plurality of sensor cells.

In this embodiment as explained above, the potential control circuit 150 controls the potential of the surface (node N2) of the finger 3 via the capacitance Cc formed between the surface of the finger 3 and the high-sensitivity electrode 103, so it is possible to control the potential at the node N2 when the resistance Rf of the finger 3 is high, and increase the sensitivity of detection of the capacitance Cf.

Note that although the potential at the node N3 is changed in accordance with the control signal S2 in this embodiment, what is important is to change the potential at the node N3 in the opposite direction to the potential change at the node N1, so the method is not limited to the use of the control signal S2, and the timing at which the potential at the node N3 is changed is not limited to the period after time t2.

Note also that in this embodiment, a signal obtained by storing an electric charge in the node N1 and then removing this electric charge is used as the output from the sensor cell. However, it is also possible to use, as the output from the sensor cell, a signal obtained by removing the electric charge from the node N1 and then storing an electric charge in the node N1. In this case, the potential Vp shown in FIG. 7 is set at the ground potential to allow the switch SW1 to function as a discharging circuit. In addition, the switch SW3 is caused to select the ground potential GND when the switch SW1 is closed and select the power supply potential VDD when the switch SW1 is open, thereby storing an electric charge in the node N1. In this arrangement, if the resistance Rf is high because, e.g., the finger 3 is dry, the potential at the node N2 rises in accordance with the potential change at the node N1 when an electric charge is stored in the node N1. To prevent this, the potential control circuit 150 changes the potential at the node N3 in the opposite direction to the potential change at the node N1. That is, the potential at the node N3 is decreased. More specifically, it is only necessary to cause the switch SW5 to select the potential V2 when the switch SW1 is closed, and select the potential V1 (V1<V2) when the switch SW1 is open.

Third Embodiment

The third embodiment of the present invention will be described below.

Figure 11:
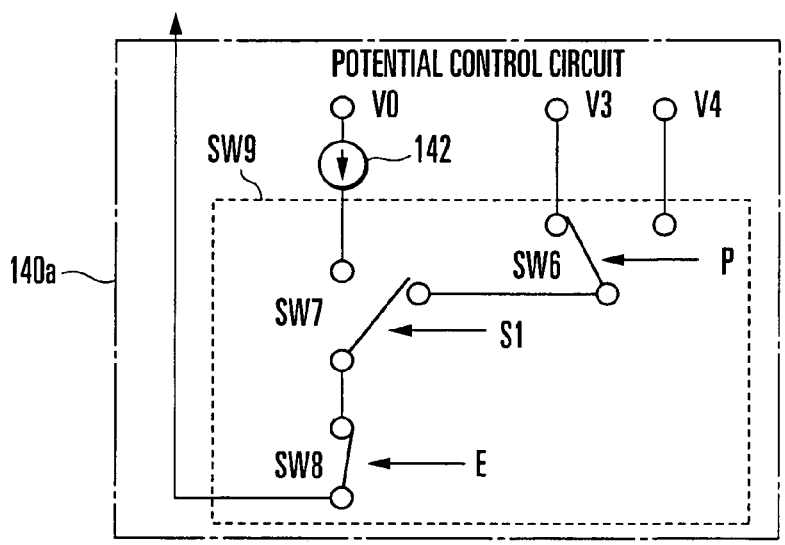
FIG. 11 is a block diagram showing an implementation example of a potential control circuit of a surface shape recognizing sensor device according to the third embodiment of the present invention.

A surface shape recognizing sensor device according to the third embodiment of the present invention uses a potential control circuit 140a shown in FIG. 11 instead of the potential control circuit 140 shown in FIG. 2 of the first embodiment. The potential control circuit 140a includes a current source 142 which stores an electric charge in a node N3 as a connecting point between the output of the potential control circuit 140a and a high-sensitivity electrode 103, a switch SW6 which selects a predetermined potential V3 (sixth potential) or V4 (fifth potential), a switch SW7 which selects the output of the current source 142 or switch SW6, and a switch SW8 which controls an electrical connection between the output of the switch SW7 and the high-sensitivity electrode 103. The switches SW6 to SW8 form a second switching element SW9.

The operation of the surface shape recognizing sensor device of this embodiment when Rf>>0 will be explained below with reference to FIGS. 12A to 12E.

The basic operation is the same as the operation of the first embodiment shown in FIGS. 4A to 4E. The difference from FIGS. 4A to 4E is the operation of the potential control circuit 140a. The switch SW6 selects the potential V4 when a control signal P is Low level, and the potential V3 (V3<V4) when the control signal P is High level. The switch SW7 selects the output of the switch SW6 when a control signal Si is Low level, and the output of the current source 142 when the control signal S1 is High level. The switch SW8 is turned on by a control signal E during a period before time t3 in FIG. 12B, and opened at time t3. Since the switches SW6 to SW8 thus operate, the high-sensitivity electrode 103 can be set at the potential V4 before charging to a node N1 between the output of a signal generating circuit 11 and a sensor electrode 101 is started, set at the potential V3 when the charging is started, and connected to the current source 142 to store an electric charge after the charging is completed.

Figure 12A:
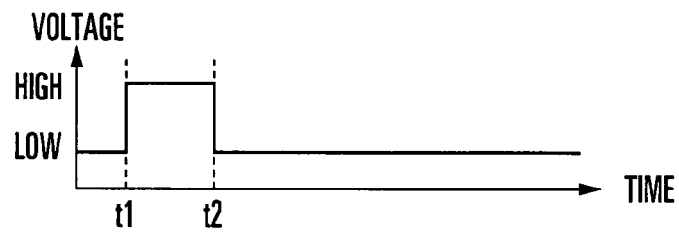
FIG. 12A is one of timing charts for explaining the operation of the surface shape recognizing sensor device using the potential control circuit shown in FIG. 11 when the resistance of a finger is high, in which the change in control signal P with time is shown.
Figure 12B:
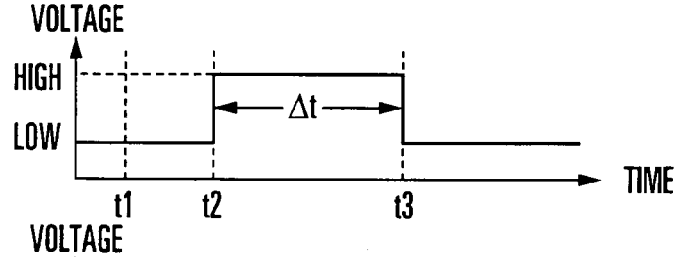
FIG. 12B is one of the timing charts for explaining the operation of the surface shape recognizing sensor device using the potential control circuit shown in FIG. 11 when the resistance of a finger is high, in which the change in control signal S1 with time is shown.
Figure 12C:
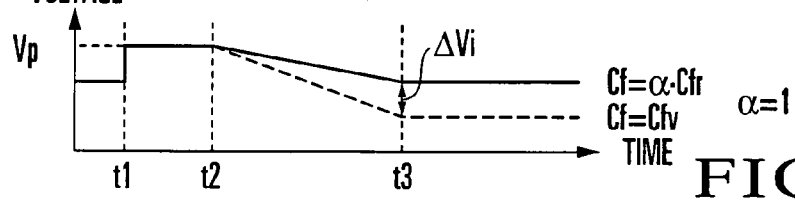
FIG. 12C is one of the timing charts for explaining the operation of the surface shape recognizing sensor device using the potential control circuit shown in FIG. 11 when the resistance of a finger is high, in which the change in potential at a node N1 is shown.
Figure 12D:
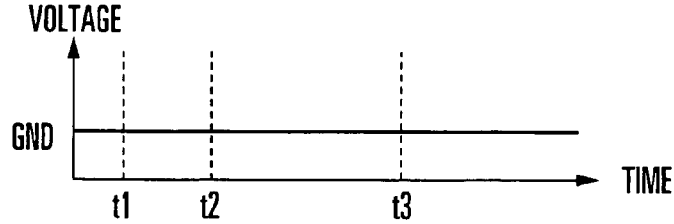
FIG. 12D is one of the timing charts for explaining the operation of the surface shape recognizing sensor device using the potential control circuit shown in FIG. 11 when the resistance of a finger is high, in which the change in potential at a node N2 is shown.
Figure 12E:
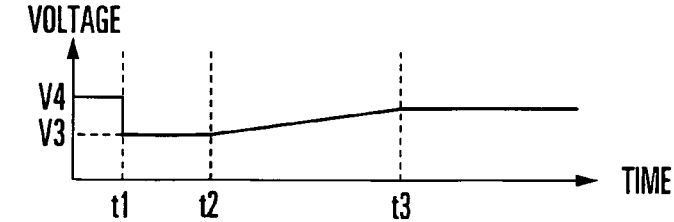
FIG. 12E is one of the timing charts for explaining the operation of the surface shape recognizing sensor device using the potential control circuit shown in FIG. 11 when the resistance of a finger is high, in which the change in potential at a node N3 is shown.

In this embodiment, it is possible not only to suppress the potential fluctuation at a node N2 during a period from time t2 to time t3 in the same manner as in FIGS. 4A to 4E, but also to suppress the potential fluctuation at the node N2 at time t1 as shown in FIG. 12D by changing the potential at the node N3 in the opposite direction to the potential change at the node N1 at the charge timing of the node N1 at time t1 as shown in FIG. 12E. As a consequence, the potential at the node N2 can be controlled in all the periods, and the effective reduction in capacitance Cf caused by the potential fluctuation at the node N2 can be prevented more effectively than in the first embodiment.

In this embodiment as described above, the potential control circuit 140a controls the potential of the surface (node N2) of a finger 3 via a capacitance Cc formed between the surface of the finger 3 and the high-sensitivity electrode 103, so it is possible to control the potential at the node N2 when a resistance Rf of the finger 3 is high, and increase the sensitivity of detection of the capacitance Cf.

Note that in this embodiment, as in the first embodiment, a signal obtained by removing the electric charge from the node N1 and then storing an electric charge in the node N1 for only a predetermined time may also be output from a sensor cell. In this case, the current source 142 is connected in the opposite direction to that shown in FIG. 11. In addition, the high-sensitivity electrode 103 is set at the potential V3 before discharging of the node N1 is started, set at the potential V4 (V3<V4) when the discharging is started, and connected to the current source 142 to remove an electric charge after the discharging is completed.

Fourth Embodiment

The fourth embodiment of the present invention will be described below.

Figure 13A:
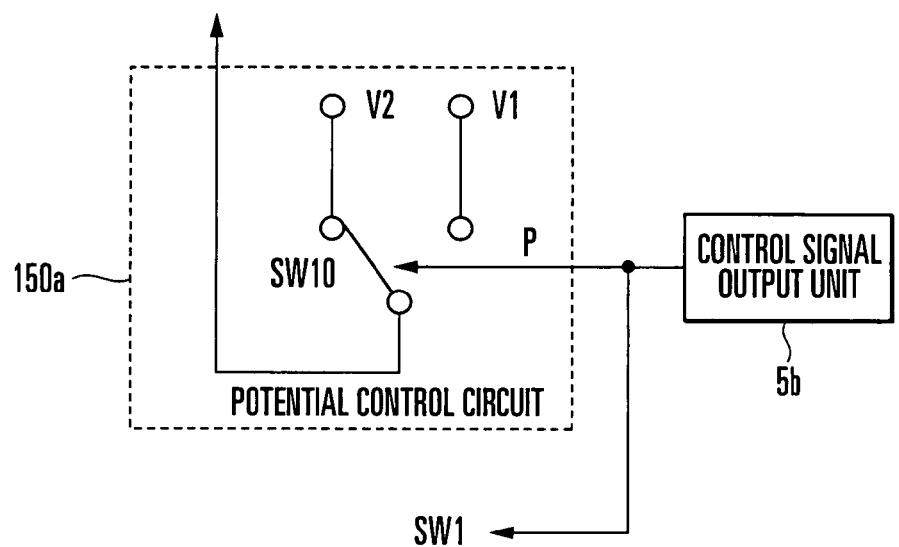
FIG. 13A is a block diagram showing an implementation example of a potential control circuit of a surface shape recognizing sensor device according to the fourth embodiment of the present invention.

A surface shape recognizing sensor device of the fourth embodiment of the present invention uses a potential control circuit 150a shown in FIG. 13A instead of the potential control circuit 150 shown in FIG. 7 of the second embodiment. The potential control circuit 150a has a switch SW10 (setting unit) which selects a predetermined potential V1 (eighth potential) or V2 (seventh potential, ninth potential), and outputs the selected potential to a high-sensitivity electrode 103. While the control signal S2 is used in the potential control circuit 150 shown in FIG. 9A, a control signal P is used in this embodiment. That is, in this embodiment, a switch SW1 (charging circuit) and the potential control circuit 150a are together controlled by a control signal P input from a control signal output circuit 5a.

The operation of the surface shape recognizing sensor device of this embodiment when Rf>>0 will be explained below with reference to FIGS. 14A to 14E.

The basic operation is the same as the operation of the second embodiment shown in FIGS. 8A to 8E. The difference from FIGS. 8A to 8E is the operation of the potential control circuit 150a. The switch SW10 selects the potential V2 when the control signal P is Low level, and the potential V1 when the control signal P is High level. Since the switch SW10 thus operates, the high-sensitivity electrode 103 can be set at the potential V2 before charging to a node N1 between the output of a signal generating circuit 13 and a sensor electrode 101 is started, at the eighth potential V1 when the charging is started, and at the potential V2 after the charging is completed, thereby generating a waveform shown in FIG. 14E.

Figure 14A:
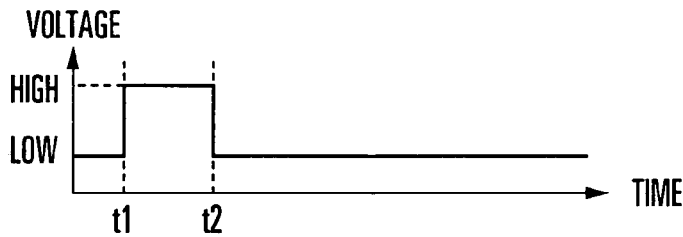
FIG. 14A is one of timing charts for explaining the operation of the surface shape recognizing sensor device using the potential control circuit shown in FIG. 13 when the resistance of a finger is high, in which the change in control signal P with time is shown.
Figure 14B:
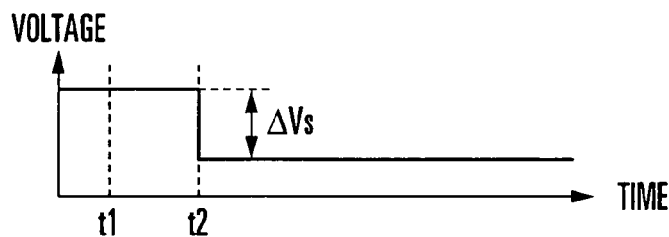
FIG. 14B is one of the timing charts for explaining the operation of the surface shape recognizing sensor device using the potential control circuit shown in FIG. 13 when the resistance of a finger is high, in which the change in driving voltage Vs of the capacitive element Cs with time is shown.
Figure 14C:
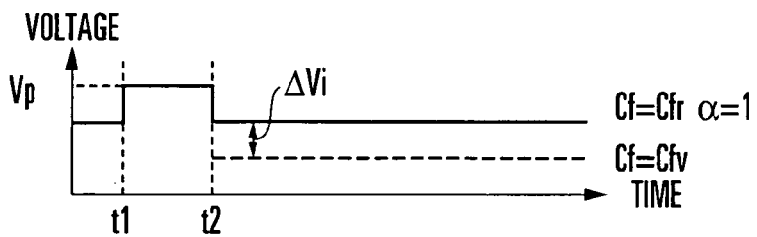
FIG. 14C is one of the timing charts for explaining the operation of the surface shape recognizing sensor device using the potential control circuit shown in FIG. 13 when the resistance of a finger is high, in which the change in potential at a node N1 is shown.
Figure 14D:
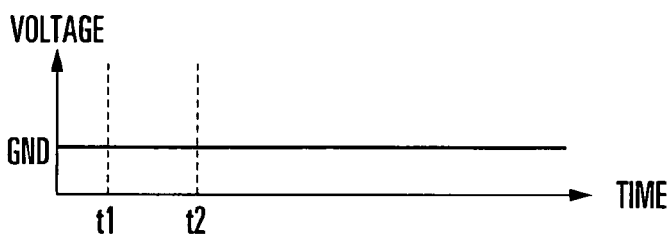
FIG. 14D is one of the timing charts for explaining the operation of the surface shape recognizing sensor device using the potential control circuit shown in FIG. 13 when the resistance of a finger is high, in which the change in potential at a node N2 is shown.
Figure 14E:
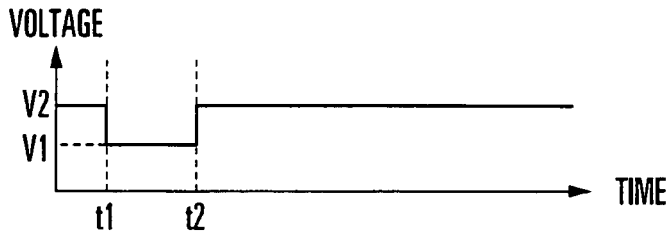
FIG. 14E is one of the timing charts for explaining the operation of the surface shape recognizing sensor device using the potential control circuit shown in FIG. 13 when the resistance of a finger is high, in which the change in potential at a node N3 is shown.

In this embodiment, it is possible not only to suppress the potential fluctuation at a node N2 during a period after time t2 in the same manner as in FIGS. 8A to 8E, but also to suppress the potential fluctuation at the node N2 at time t1 as shown in FIG. 14D by changing the potential at the node N3 in the opposite direction to the potential change at the node N1 at the charge timing of the node N1 at time t1 as shown in FIG. 14E. As a consequence, the potential at the node N2 can be controlled in all the periods, and the effective reduction in capacitance Cf caused by the potential fluctuation at the node N2 can be prevented more effectively than in the second embodiment.

Note that the potential before t1 and the potential after t2 at the node N3 are set at V2, but these potentials are not limited to V2, and the potential (seventh potential) before t1 and the potential (ninth potential) after t2 may also be different. In this case, another power supply is prepared in addition to the potentials V1 and V2 shown in FIG. 13A, and control is so performed as to switch these potentials.

Figure 13B:
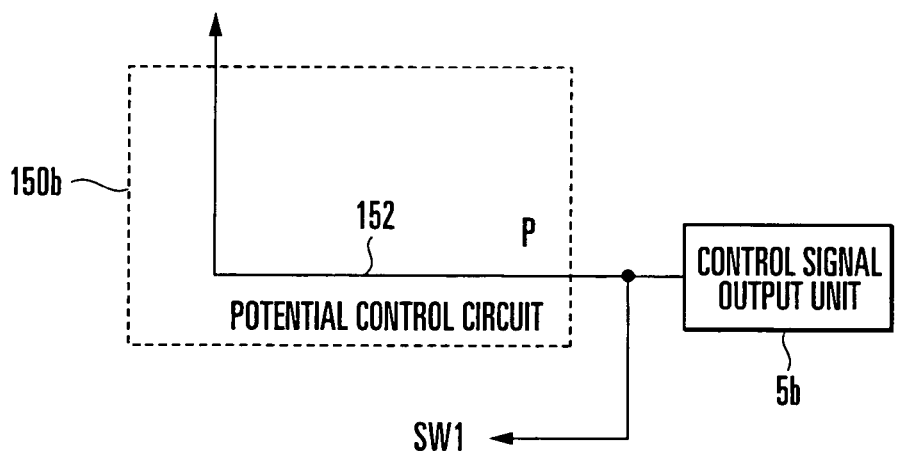
FIG. 13B is a block diagram showing another implementation example of the potential control circuit of the surface shape recognizing sensor device according to the fourth embodiment of the present invention.

A potential control circuit 150b shown in FIG. 13B may also be used in place of the potential control circuit 150a shown in FIG. 13A. The potential control circuit 150b has a signal line 152 (setting unit) which supplies the control signal P to the high-sensitivity electrode 103. Since the potential of the control signal P is directly used, the potential control circuit 150*b* can be implemented without using any additional circuit.

In this embodiment as explained above, the potential control circuit 150*a* or 150*b* controls the potential of the surface (node N2) of a finger 3 via a capacitance Cc formed between the surface of the finger 3 and the high-sensitivity electrode 103, so it is possible to control the potential at the node N2 when a resistance Rf of the finger 3 is high, and increase the sensitivity of detection of the capacitance Cf.

Note that in this embodiment, as in the second embodiment, a signal obtained by removing the electric charge from the node N1 and then storing an electric charge in the node N1 may also be output from a sensor cell. In this case, as shown in FIG. 13A, for example, the high-sensitivity electrode 103 need only be set at the potential V1 before discharging of the node N1 is started, at the potential V2 (V1<V2) when the discharging is started, and at the potential V1 after the discharging is completed.

Fifth Embodiment

The fifth embodiment of the present invention will be described below.

Figure 15:
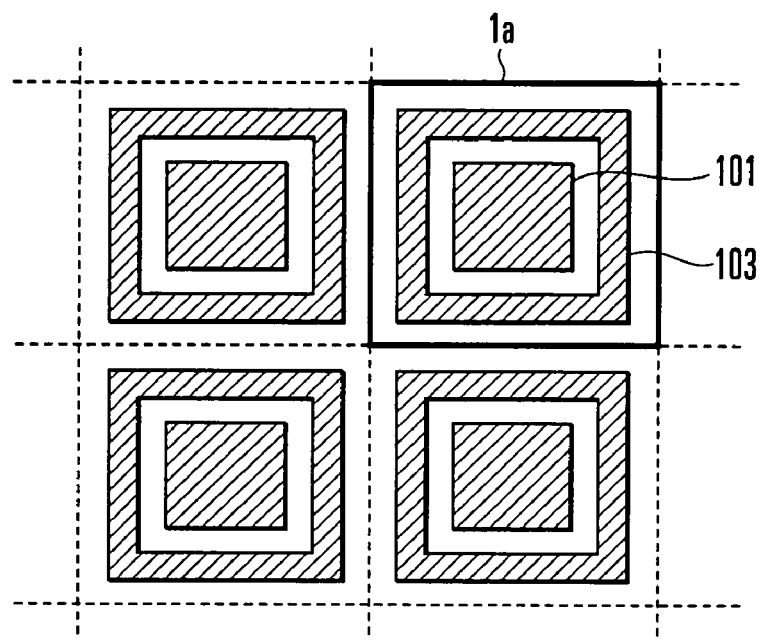
FIG. 15 is a plan view showing the layout pattern of sensor electrodes and high-sensitivity electrodes in a sensor cell array according to the fifth embodiment of the present invention.

In a sensor cell array according to the fifth embodiment of the present invention, sensor electrodes 101 and high-sensitivity electrodes 103 are arranged differently from FIGS. 3A and 3B. That is, as shown in FIG. 15, the high-sensitivity electrode 103 is so formed as to surround the sensor electrode 101. In this arrangement, noise from an adjacent sensor cell to the sensor electrode 101 can be reduced. The arrangement shown in FIG. 15 can be applied to all the first to fourth embodiments.

Sixth Embodiment

The sixth embodiment of the present invention will be described below.

Figure 16:
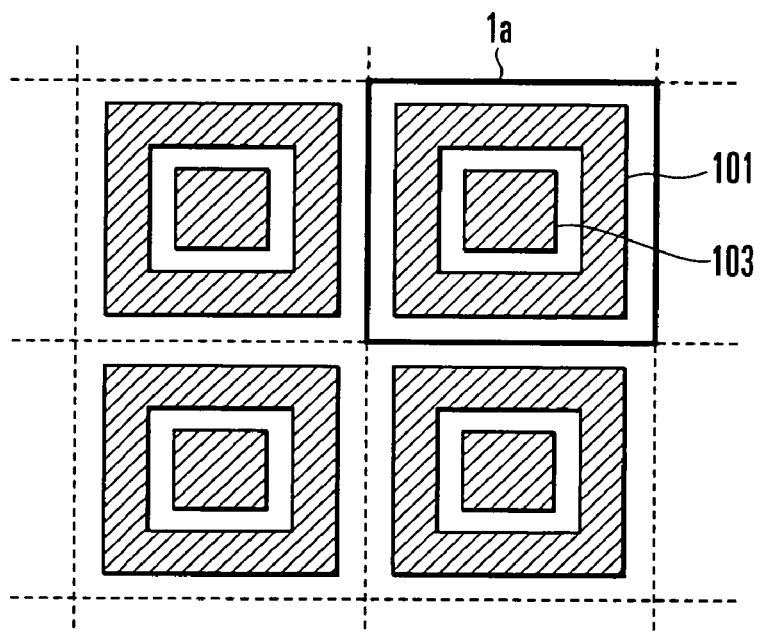
FIG. 16 is a plan view showing the layout pattern of sensor electrodes and high-sensitivity electrodes in a sensor cell array according to the sixth embodiment of the present invention.

In a sensor cell array according to the sixth embodiment of the present invention, sensor electrodes 101 and high-sensitivity electrodes 103 are arranged differently from FIGS. 3A, 3B, and 15. That is, as shown in FIG. 16, the sensor electrode 101 is so formed as to surround the high-sensitivity electrode 103. In this arrangement, the potential of the finger surface in each sensor cell can be efficiently controlled while the influence from an adjacent sensor cell is reduced. The arrangement shown in FIG. 16 can be applied to all the first to fourth embodiments.

Seventh Embodiment

The seventh embodiment of the present invention will be described below.

In a sensor cell array according to the seventh embodiment of the present invention, the formation positions of a sensor electrode and high-sensitivity electrode with respect to the substrate surface are different.

Figure 17A:
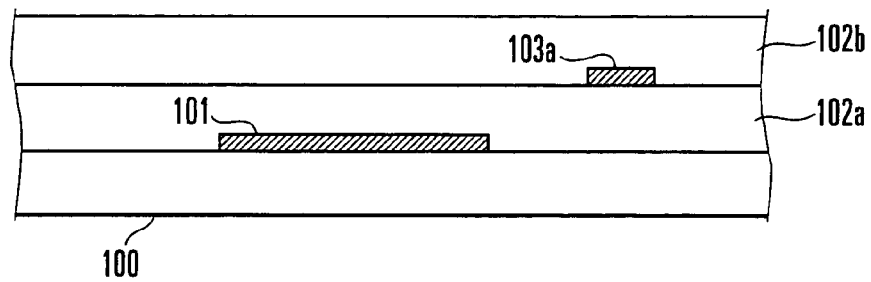
FIG. 17A is a sectional view showing examples of the formation positions of a sensor electrode and high-sensitivity electrode in a sensor cell array according to the seventh embodiment of the present invention.

FIG. 17A shows an example in which a high-sensitivity electrode 103*a* is formed in a position higher than a sensor electrode 101. More specifically, the sensor electrode 101 is formed on an insulating film 100 on a substrate, a first passivation film 102*a* is formed on the insulating film 100 so as to cover the sensor electrode 101, the high-sensitivity electrode 103*a* is formed on the first passivation film 102*a*, and a second passivation film 102*b* is formed on the first passivation film 102*a* so as to cover the high-sensitivity electrode 103*a*. The sensor electrode 101 and high-sensitivity electrode 103*a* are so formed as not to face each other. By using a plurality of passivation films as described above, the sensor electrode 101 and high-sensitivity electrode 103*a* can be easily formed at different heights.

When the high-sensitivity electrode 103*a* is formed in a position higher than the sensor electrode 101, the distance between the surface of a finger 3 in contact with the second passivation film 102*b* and the high-sensitivity electrode 103*a* becomes smaller than that when the sensor electrode 101 and high-sensitivity electrode 103 are formed at the same height as shown in FIG. 2 or the like. When the distance is 1/N (N>1), for example, a capacitance Cc formed between the surface of the finger 3 and the high-sensitivity electrode 103*a* can be maintained even if the area of the high-sensitivity electrode 103*a* is 1/N that of the high-sensitivity electrode 103 shown in FIG. 2 or the like. That is, since the capacitance Cc can be maintained even when the high-sensitivity electrode 103*a* is downsized, it is possible to obtain the same effect of controlling the potential of the finger surface (node N2) as in the first to fourth embodiments. Also, when the high-sensitivity electrode 103*a* is downsized as shown in FIG. 17A, it is possible to increase the area of the sensor electrode 101, and consequently increase the detection sensitivity.

Figure 17B:
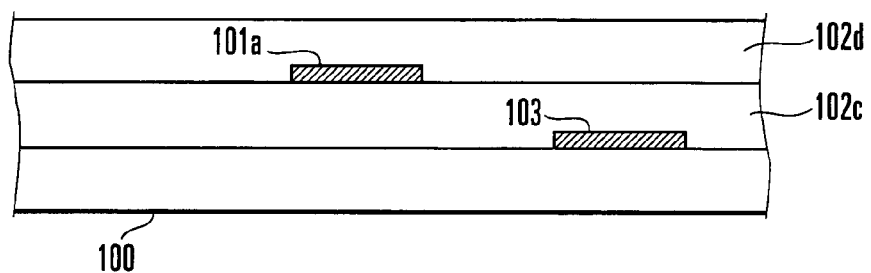
FIG. 17B is a sectional view showing other examples of the formation positions of the sensor electrode and high-sensitivity electrode in the sensor cell array according to the seventh embodiment of the present invention.
Figure 18:
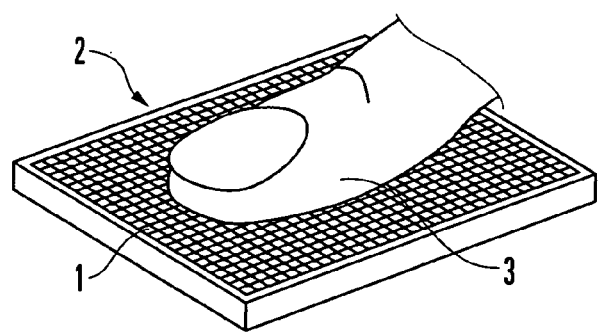
FIG. 18 is a perspective view of a conventional capacitive fingerprint sensor in which sensor cells are formed into a lattice shape.
Figure 19:
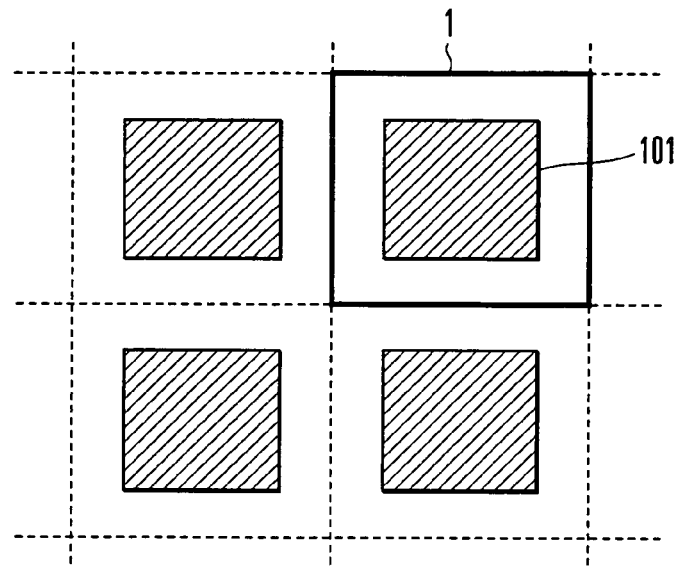
FIG. 19 is a plan view showing the layout pattern of sensor electrodes in a sensor cell array shown in FIG. 18.

Furthermore, as shown in FIG. 17B, a sensor electrode 101*a* may also be formed in a position higher than a high-sensitivity electrode 103. Referring to FIG. 17B, the high-sensitivity electrode 103 is formed on an insulating film 100 on a substrate, a first passivation film 102*c* is formed on the insulating film 100 so as to cover the high-sensitivity electrode 103, the sensor electrode 101*a* is formed on the first passivation film 102*c*, and a second passivation film 102*d* is formed on the first passivation film 102*c* so as to cover the sensor electrode 101*a*. The sensor electrode 101*a* and high-sensitivity electrode 103 are so formed as not to face each other. In this arrangement, the sensor electrode 101*a* can be downsized while a capacitance Cf formed between the surface of the finger 3 and the sensor electrode 101*a* is maintained. Accordingly, it is possible to increase the area of the sensor electrode 101, and consequently increase the detection sensitivity.

Note that in FIGS. 17A and 17B, the surfaces of the passivation films 102*b* and 102*d* are desirably planarized.

INDUSTRIAL APPLICABILITY

The present invention is applicable to, e.g., a capacitive fingerprint sensor.

The invention claimed is:

1. A surface shape recognizing sensor device characterized by comprising:

a plurality of sensor cells which are two-dimensionally arranged, detect capacitances corresponding to ridges and valleys of a surface of an object to be recognized, and output signals corresponding to the capacitances; and a signal processor which calculates a surface shape of the object on the basis of the signals input from said sensor cells, said sensor cell comprising:

a substrate;

a first electrode formed on said substrate;

a signal output unit which outputs a signal corresponding to a capacitance formed between said first electrode and the surface of the object;

a second electrode formed on said substrate so as to be insulated and isolated from said first electrode; and a potential controller which controls a potential of the surface of the object via a capacitance formed between said second electrode and the surface of the object by controlling a potential of said second electrode.

2. A surface shape recognizing sensor device according to claim 1, characterized in that said signal output unit comprises:
a signal generating circuit which generates a voltage signal corresponding to the capacitance formed between said first electrode and the surface of the object;
a charging/discharging circuit which performs one of storage and removal of an electric charge with respect to a node as a connecting point between said first electrode and an output of said signal generating circuit, before the signal is generated by said signal generating circuit; and
a detection circuit which detects the voltage signal output from said signal generating circuit to the node after one of the storage and removal of an electric charge is performed, and outputs the voltage signal as an output from said signal output unit.

3. A surface shape recognizing sensor device according to claim 2, characterized in that said potential controller comprises a potential control circuit which changes the potential of said second electrode in an opposite direction to a change in voltage signal output from said signal generating circuit.

4. A surface shape recognizing sensor device according to claim 2, characterized in that said potential controller comprises a potential control circuit which changes the potential of said second electrode in an opposite direction to a potential change when one of charging and discharging of the node is performed, and to a change in voltage signal output from said signal generating circuit.

5. A surface shape recognizing sensor device according to claim 1, characterized in that said signal output unit comprises:
a signal generating circuit which generates a voltage signal corresponding to the capacitance formed between said first electrode and the surface of the object;
a charging circuit which stores an electric charge in a node as a connecting point between said first electrode and an output of said signal generating circuit, before the signal is generated by said signal generating circuit; and
a detection circuit which detects the voltage signal output from said signal generating circuit to the node after the electric charge is stored, and outputs the voltage signal as an output from said signal output unit.

6. A surface shape recognizing sensor device according to claim 5, characterized in that
said signal generating circuit comprises:
a first current source which removes the electric charge from the node; and
a first switching element which is placed between the node and said first current source, and generates a voltage signal by connecting the node and said first current source for only a predetermined period after an electric charge is stored in the node, and
said potential controller comprises:
a second current source which charges said second electrode; and
a second switching element which is placed between said second electrode and said second current source, and controls the potential of said second electrode by connecting said second electrode and said second current source.

7. A surface shape recognizing sensor device according to claim 6, characterized by further comprising a control signal output unit which outputs a control signal which controls said first switching element and said second switching element together.

8. A surface shape recognizing sensor device according to claim 5, characterized in that
said signal generating circuit comprises:
a capacitive element including a first terminal and a second terminal, the first terminal being connected to the node; and
a third switching element which sets the second terminal of said capacitive element at a first potential before charging to the node is completed, and sets the second terminal at a second potential lower than the first potential after the charging is completed, thereby generating a voltage signal from said capacitive element, and
said potential controller comprises a setting unit which sets said second electrode at a third potential before the charging to the node is completed, and sets said second electrode at a fourth potential higher than the third potential after the charging is completed, thereby controlling the potential of said second electrode.

9. A surface shape recognizing sensor device according to claim 8, characterized by further comprising a control signal output unit which outputs a control signal which controls said third switching element and said setting unit together.

10. A surface shape recognizing sensor device according to claim 5, characterized in that
said signal generating circuit comprises:
a first current source which removes the electric charge from the node; and
a first switching element which is placed between the node and said first current source, and generates a voltage signal by connecting the node and said first current source for only a predetermined period after an electric charge is stored in the node, and
said potential control circuit comprises:
a second current source which charges said second electrode; and
a second switching element which sets said second electrode at a fifth potential before charging to the node is started, sets said second electrode at a sixth potential lower than the fifth potential when the charging is started, and then connects said second electrode and said second current source, thereby controlling the potential of said second electrode.

11. A surface shape recognizing sensor device according to claim 5, characterized in that
said signal generating circuit comprises:
a capacitive element including a first terminal and a second terminal, the first terminal being connected to the node; and
a third switching element which sets the second terminal of said capacitive element at a first potential before charging to the node is completed, and sets the second terminal at a second potential lower than the first potential after the charging is completed, thereby generating a voltage signal from said capacitive element, and
said potential control circuit comprises a setting unit which sets said second electrode at a seventh potential before the charging to the node is started, sets said second electrode at an eighth potential lower than the seventh potential when the charging is started, and sets said second electrode at a ninth potential higher than the eighth potential after the charging is completed, thereby controlling the potential of said second electrode.

12. A surface shape recognizing sensor device according to claim 11, characterized by further comprising a control signal output unit which outputs a control signal which controls said charging circuit and said setting unit together.

13. A surface shape recognizing sensor device according to claim 1, characterized in that said second electrode is formed to surround said first electrode.

14. A surface shape recognizing sensor device according to claim 1, characterized in that said first electrode is formed to surround said second electrode.

15. A surface shape recognizing sensor device according to claim 1, characterized in that an area of said second electrode is not more than an area of said first electrode.

16. A surface shape recognizing sensor device according to claim 15, characterized in that the area of said second electrode is smaller than the area of said first electrode.

17. A surface shape recognizing sensor device according to claim 1, characterized in that said second electrode is formed at a height different from said first electrode with respect to a surface of said substrate.

* * * * *